US007741541B2

(12) United States Patent  
Bisht et al.

(10) Patent No.: US 7,741,541 B2
(45) Date of Patent: Jun. 22, 2010

(54) METHOD FOR OBTAINING IMPROVED FERTILITY RESTORER LINES FOR TRANSGENIC MALE STERILE CROP PLANTS AND A DNA CONSTRUCT FOR USE IN SAID METHOD

(75) Inventors: Naveen Chandra Bisht, New Delhi (IN); Arun Jagannath, Delhi (IN); Vibha Gupta, New Delhi (IN); Pradeep Kumar Burma, New Delhi (IN); Deepak Pental, New Delhi (IN)

(73) Assignees: University of Delhi South Campus, New Delhi (IN); Dhara Vegetable Oil and Foods Company Limited, Gujara (IN)

( * ) Notice: Subject to any disclaimer, the term of this patent is extended or adjusted under 35 U.S.C. 154(b) by 728 days.

(21) Appl. No.: 10/563,571

(22) PCT Filed: Jul. 7, 2003

(86) PCT No.: PCT/IN03/00235

§ 371 (c)(1),
(2), (4) Date: Jun. 8, 2006

(87) PCT Pub. No.: WO2005/003361

PCT Pub. Date: Jan. 13, 2005

(65) Prior Publication Data

US 2007/0061912 A1    Mar. 15, 2007

(51) Int. Cl.
*C12N 15/82* (2006.01)
*C12N 15/84* (2006.01)
*C12N 15/31* (2006.01)
*C12N 15/55* (2006.01)
*A01H 5/00* (2006.01)
*A01H 5/10* (2006.01)

(52) U.S. Cl. ............... 800/303; 800/287; 800/288; 800/294; 800/300; 800/306; 435/6; 435/199; 435/469

(58) Field of Classification Search .................. None
See application file for complete search history.

(56) References Cited

U.S. PATENT DOCUMENTS

| 5,378,619 | A | * | 1/1995 | Rogers ................ 800/294 |
| 5,750,867 | A | * | 5/1998 | Williams et al. .......... 800/274 |
| 5,962,769 | A | | 10/1999 | Albertsen et al. |
| 6,147,282 | A | | 11/2000 | Goff et al. |
| 6,162,964 | A | * | 12/2000 | Fabijanski et al. ......... 800/274 |
| 6,207,881 | B1 | | 3/2001 | Theologis et al. |
| 6,372,960 | B1 | | 4/2002 | Michiels et al. |
| 2006/0191038 | A1 | * | 8/2006 | Flasinski ................ 800/285 |

FOREIGN PATENT DOCUMENTS

WO    WO 97/46690    * 12/1997

OTHER PUBLICATIONS

Jagannath et al. Current Science 82(1): 46-52 (Jan. 2002).*
Williams et al. 1998. Sequence No. 17 of US 5,750,867.*
Shah et al. Proc. Natl. Acad. Sci. USA 79: 1022-1026 (Feb. 1982).*
Jofuku et al. The Plant Cell 1: 1079-1093 (Nov. 1989).*
Stevenson et al. Nucleic Acids Research 14(21): 8307-8330 (1986).*
Dey et al. Plant Molecular Biology 40(5): 771-782 (Jul. 1999).*
Que & Jorgensen, "Homology-Based Control of Gene Expression Patterns in Transgenic Petunia Flowers," Dev. Genet., vol. 22, 1998, pp. 100-109, Wiley-Liss, Inc. New York.
Mol et al., "Genetic Manipulation of Floral Pigmentation Genes," Plant Mol. Biol., vol. 13, 1989, pp. 287-294, Kluwer Academic, Dordrecht, Holland.
Matzke et al., "Differential Inactivation and Methylation of a Transgene in Plans by Two Suppressor Loci Containing Homologous Sequences," Plant Mol. Biol., Vo. 16, 1991, pp. 821-830, Kluwer Academic, Dordrecht, Holland.
Adang et al., "The Reconstruction and Expression of a *Bacillus thuringiensis* cryIIIA Gene in Protoplasts and Potato Plants," Plant Mol. Biol., vol. 21, 1993, pp. 1131-1145, Kluwer Academic, Dordrecht, Holland.
Koziel et al., "Field Performance of Elite Transgenic Maize Plants Expressing an Insecticidal Protein Derived from *Bacillus thuringiensis*," Bio/Technology, vol. 11, 1993, pp. 194-200, Nature Publishing Co., New York, NY.
Wosnick et al, "Total Chemical Synthesis and Expression in *Escherichia coli* of a Maize Glutathione-Transferase GST1 Gene," Gene, vol. 76, 1989, pp. 153-160, Elsevier, Amsterdam, Holland.
Adams et al., "Synthesis of a Gene for the HIV Transactivator TAT by a Novel Single Stranded Approach Involving in vivo Gap Repair," Nucleic Acids Res., vol. 16, 1988, pp. 4287-4298, Oxford University Press, Oxford, England.
Kozak, "Point Mutations Define a Sequence Flanking the AUG Initiator Codon That Modulates Translation by Eukaryotic Ribosomes," Cell, vol. 44, 1986, pp. 283-292, Cell Press, Cambridge, MA.
Murray et al., "Codon Usage in Plant Genes," Nucleic Acids Research, vol. 17, 1989, pp. 480-498, Oxford University Press, Oxford, England.
Pradhan et al., "Heterosis Breeding in Indian Mustard (*Brassica juncea* L. Czern & Coss): Analysis of Component Characters Contributing to Heterosis for Yield," Euphytica, vol. 69, 1993, pp. 219-229, Kluwer Academic, Dordrecht, Holland.

(Continued)

*Primary Examiner*—David T Fox
(74) *Attorney, Agent, or Firm*—Drinker Biddle & Reath LLP

(57) ABSTRACT

A method for obtaining improved fertility restorer lines for male sterile crop plants and a DNA construct for use in said method are disclosed. The invention relates to the simultaneous use of two different gene sequences encoding the same protein product, one being the naturally occurring wild type sequence and the other sequence being generated by modification of the wild type sequence for expression in crop plants by using codon degeneracy to avoid homology between the two sequences at the DNA and mRNA levels, each of the said sequences being placed under independent transcriptional control of different overlapping plant tissue-specific regulatory elements in the same DNA construct.

30 Claims, 9 Drawing Sheets

OTHER PUBLICATIONS

Figure 1:
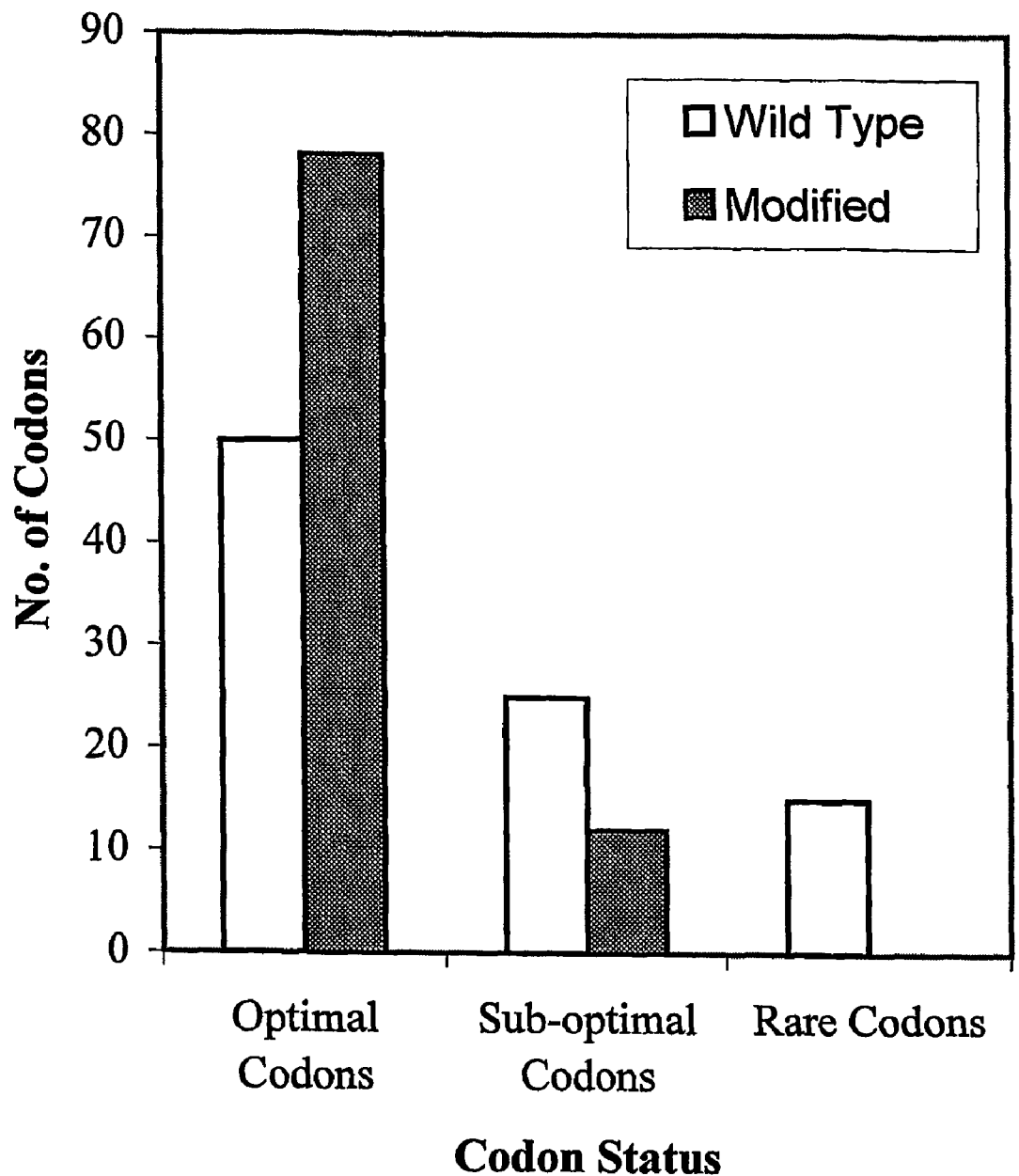

Meyer & Heidmann, "Epigenetic Variants of a Transgenic Petunia Line Show Hypermethylation in Transgene DNA: An Indication for Specific Recognition of Foreign DNA in Transgenic Plants," Mol. Gen. Genet., vol. 243, 1994, pp. 390-399, Springer Verlag, Berlin, Germany.

Wada et al., "Codon Usage Tabulated from the GenBank Genetic Sequence Data," Nucleic Acids Res., vol. 20, Supp., 1992, pp. 2111-2118, Oxford University Press, Oxford, England.

Kilby et al, "Promoter Methylation and Progressive Transgene Inactivation in *Arabidopsis*," Plant Mol. Biol., vol. 20, 1992, pp. 103-112, Kluwer Academic, Dordrecht, Holland.

Paul et al., "The Isolation and Characterization of the Tapetum-Specific *Arabidopsis thaliana* A9 Gene," Plant Mol. Biol., vol. 19, 1992, pp. 611-622, Kluwer Academic, Dordrecht, Holland.

Hartley, "Barnase and Barstar: Two Small Proteins to Fold and Fit Together," Trends Biochem. Sci., vol. 14, 1989, pp. 450-454, Elsevier, Cambridge, England.

McVetty et al., "The Significance of Floral Characteristics in See Production of Four Summer Rape Cultivar A-Lines with *pol* Cytoplasm," Can. J. Plant Sci., vol. 69, 1989, pp. 915-918, Agricultural Institute of Canada, Ottawa, Canada.

Mariani et al., "Induction of Male Sterility in Plants by a Chimaeric Ribonuclease Gene," Nature, vol. 347, 1990, pp. 737-741, Nature Publishing Group, London, England.

Mariani et al., "A Chimaeric Ribonuclease-Inhibitor Gene Restores Fertility to Male Sterile Plants," Nature, vol. 357, 1992, pp. 384-387, Nature Publishing Group, London, England.

Goodall & Filipowicz., "The AU-Rich Sequences Present in the Introns of Plant Nuclear Pre-mRNAs Are Required for Splicing," Cell, vol. 58, 1999, pp. 473-483, Cell Press, Cambridge, MA.

Williams, "Genetic Engineering for Pollination Control," Trends Biotechnol., vol. 13, 1995, pp. 344-349, Barking Elsevier Science, Amsterdam, Holland.

Meyer & Saedler, "Homology-Dependent Gene Silencing in Plants," Annu. Rev. Plant Physiol. Plant Mol. Biol., vol. 42, 1996, pp. 23-48, Annual Reviews Inc., Palo Alto, CA.

Matzke et al., "Homology-Dependent Gene Silencing in Transgenic Plants: Epistatic Silencing Loci Contain Multiple Copies of Methylated Transgenes," Mol. Gen. Genet., vol. 244, 1994, pp. 219-229, Springer Verlag, Berlin, Germany.

Vaucheret & Fagard, "Transcriptional Gene Silencing in Plants: Targets, Inducers and Regulators," Trends Genet., vol. 17, 2001, pp. 29-35, Elsevier, Cambridge, MA.

van der Krol et al., "Flavonoid Genes in Petunia: Addition of a Limited Number of Gene Copies May Lead to a Suppression of Gene Expression," Plant Cell, vol. 2, 1990, pp. 291-299, American Society of Plant Physiologists, Rockville, MD.

Napoli et al., "Introduction of a Chimeric Chalcone Synthase Gene into Petunia Results in Reversible Co-Suppression of Homologous Genes *in trans*," Plant Cell, vol. 2, 1990, pp. 279-289, American Society of Plant Physiologists, Rockville, MD.

Fire, "RNA-Triggered Gene Silencing," Trends Genet., vol. 15, 1999, pp. 358-363, Elsevier, Cambridge, MA.

Matzke & Matzke, "How and Why Do Plants Inactivate Homologous (Trans)genes?" Plant Physiol., vol. 107, 1995, pp. 679-685, American Society of Plant Physiologists, Lancaster, PA.

Hamilton & Baulcombe, "A Species of Small Antisense RNA in Posttranscriptional Gene Silencing in Plants," Science, vol. 286, 1999, pp. 950-952, American Association for the Advancement of Science, Washington, DC.

Jagannath et al., "The Use of a Spacer DNA Fragment Insulates the Tissue-Specific Expression of a Cytotoxic Gene (*barnase*) and Allows High-Frequency Generation of Transgenic Male Sterile Lines in *Brassica juncea* L.," Molecular Breeding, vol. 8, 2001, pp. 11-23, Kluwer Academic, Dordrecht, Holland.

Hartley & Smeaton, "On the Reaction between the Extracelullular Ribonuclease of *Bacillus amyloliquefaciens* (Bernase) and Its Intracellular Inhibitor (Barstar)," J. Biol. Chem., vol. 248, 1973, pp. 5624-5626, American Society for Biochemistry and Molecular Biology, Baltimore, MD.

Denis et al., "Expression of Engineered Nuclear Male Sterility in *Brassica napus*," Plant Physiol., vol. 101, 1993, p. 1295-1304, American Society of Plant Physiologists, Lancaster, PA.

Perlak et al., "Modification of the Coding Sequence Enhances Plant Expression of Insect Control Protein Genes," Proc. Natl. Acad. Sci. USA, vol. 88, 1991, pp. 3324-3328, National Academy of Sciences, Washington, DC.

Pang et al., "An Improved Green Fluorescent Protein Gene as a Vital Marker in Plants," Plant Physiol., vol. 112, 1996, pp. 893-900, American Society of Plant Physiologists, Lancaster, PA.

Strizhov et al., "A Synthetic *cryIC* Gene, Encoding a *Bacillus thuringiensis* δ-Endotoxin, Confers *Spodoptera* Resistance in Alfalfa and Tobacco," Proc. Natl. Acad. Sci. USA, vol. 91, 1996, pp. 15012-15017, National Academy of Sciences, Washington, DC.

Iannocone et al., "Specific Sequence Modifications of a *cry*3B Endotoxin Gene Result in High Levels of Expression and Insect Resistance," Plant Mol. Biol., vol. 34, 1997, pp. 485-496, Kluwer Academic, Dordrecht, Holland.

Rouwendal et al., "Enhanced Expression in Tobacco of the Gene Encoding Green Fluorescent Protein by Modification of Its Codon Usage," Plant Mol. Biol., vol. 33, 1997, pp. 989-999, Kluwer Academic, Dordrecht, Holland.

Lonsdale et al., "The Effect of Altered Codon Usage on Luciferase Activity in Tobacco, Maize and Wheat," Plant Cell Rep., vol. 17, 1998, pp. 396-399, Springer Verlag, Berlin, Germany.

Nakamura et al., "Codon Usage Tabulated from the International DNA Sequence Databases," Nucleic Acids Res., vol. 25, 1997, pp. 244-245, Oxford University Press, Oxford, England.

McClure et al., "Transcription, Organization, and Sequence of an Auxin-Regulated Gene Cluster in Soybean," Plant Cell, vol. 1, 1989, pp. 229-239, American Society of Plant Physiologists, Rockville, MD.

Ohme-Takagi et al., "The Effect of Sequences with High AU Content on mRNA Stability in Tobacco," Proc. Natl. Acad. Sci. USA, vol. 90, 1993, pp. 11811-11815, National Academy of Sciences, Washington, DC.

Dean et al., "mRNA Transcripts of Several Plant Genes are Polyadenylated at Multiple Sites in vivo," Nucleic Acids Res., vol. 14, 1986, No. 5, pp. 2229-2240, Oxford University Press, Oxford, England.

Wiebauer et al., "Nuclear Pre-mRNA Processing in Plants: Distinct Modes of 3'-Splice-Site Selection in Plants and Animals," Mol. Cell. Biol., vol. 8, 1988, pp. 2042-2051, American Society for Microbiology, Washington, DC.

Matzke et al., "Reversible Methylation and Inactivation of Marker Genes in Sequentially Transformed Tobacco Plants," EMBO J., vol. 8, 1989, pp. 643-649, Oxford University Press, Oxford, England.

Meyer et al., "Differences in DNA-Methylation are Associated with a Paramutation Phenomenon in Transgenic Petunia," Plant J., vol. 4, 1993, pp. 89-100, Blackwell Sciences, Oxford, England.

Salinas et al., "Compositional Compartmentalization and Compositional Patterns in the Nuclear Genomes of Plants," Nucleic Acids Res., vol. 16, 1988, pp. 4269-4285, Oxford University Press, Oxford, England.

Joshi, "Putative Polyadenylation Signals in Nuclear Genes of Higher Plants: A Composition and Analysis," Nucleic Acids Res., vol. 15, 1987, pp. 9627-9640, Oxford University Press, Oxford, England.

Steimer et al., "Endogenous Targets of Transcriptional Gene Silencing in *Arabidopsis*," Plant Cell, vol. 12, 2000, pp. 1165-1178, American Society of Plant Physiologists, Rockville, MD.

Seurinck et al., "The Nucleotide Sequence of Anther-Specific Gene," Nucleic Acids Res., vol. 18, 1990, pp. 3403, Oxford University Press, Oxford, England.

Kay et al., "Duplication of CaMV 35S Promoter Sequences Creates a Strong Enhancer for Plant Genes," Science, vol. 236, 1987, pp. 1299-1302, American Association for the Advancement of Science, Washington, DC.

Bhullar et al., "Strategies for Development of Functionally Equivalent Promoters with Minimum Sequence Homology for Transgene Expression in Plants: cis-Elements in a Novel DNA Context versus Domain Swapping," Plant Physiol, vol. 132, 2003, pp. 988-998, American Society of Plant Physiologists, Lancaster, PA.

* cited by examiner

ATG AAA AAA GCA GTC ATT AAC GGG GAA CAA ATC AGA AGT ATC AGC GAC

CTC CAC CAG ACA TTG AAA AAG GAG CTT GCC CTT CCG GAA TAC TAC GGT

GAA AAC CTG GAC GCT TTA TGG GAT TGT CTG ACC GGA TGG GTC GAG TAC

CCG CTC GTT TTG GAA TGG AGG CAG TTT GAA CAA AGC AAG CAG GTG AGT

GAA AAT GGC GCC GAG AGT GTG CTT CAG GTT TTC CGT GAA GCG AAA GCG

GAA GGC TGC GAC ATC ACC ATC ATA CTT TCT TAA

ATG AAG AAG GCT GTG ATC AAT GGA GAA CAA ATC AGA TCT ATC TCA GAC

CTT CAT CAA ACT TTG AAG AAG GAG CTT GCT CTT CCT GAG TAC TAT GGT

GAG AAC TTG GAC GCT TTG TGG GAT TGT CTT ACT GGA TGG GTT GAG TAC

CCT CTT GTT TTG GAA TGG AGG CAA TTC GAG CAA TCT AAG CAA CTT ACT

GAG AAT GGA GCT GAG AGC GTT CTT CAA GTG TTT AGA GAA GCT AAG GCT

GAA GGA TGT GAC ATC ACT ATC ATT CTT TCT TAA

Figure 3A

MKKAVINGEQIRSISD

LHQTLKKELALPEYYG

ENLDALWDCLTGWVEY

PLVLEWRQFEQSKQLT

ENGAESVLQVFREAKA

EGCDITIILS***

Figure 3B

```
        1 Met Lys Lys Ala Val Ile Asn Gly Glu Gln Ile Arg Ser Ile Ser Asp
wt      1 ATG AAA AAA GCA GTC ATT AAC GGG GAA CAA ATC AGA AGT ATC AGC GAC
mod       ATG AAG AAG GCT GTG ATC AAT GGA GAA CAA ATC AGA TCT ATC TCA GAC 17 Leu His Gln Thr Leu Lys Lys Glu Leu Ala Leu Pro Glu Tyr Tyr Gly
wt     49 CTC CAC CAG ACA TTG AAA AAG GAG CTT GCC CTT CCG GAA TAC TAC GGT
mod       CTT CAT CAA ACT TTG AAG AAG GAG CTT GCT CTT CCT GAG TAC TAT GGT 33 Glu Asn Leu Asp Ala Leu Trp Asp Cys Leu Thr Gly Trp Val Glu Tyr
wt     97 GAA AAC CTG GAC GCT TTA TGG GAT TGT CTG ACC GGA TGG GTC GAG TAC
mod       GAG AAC TTG GAC GCT TTG TGG GAT TGT CTT ACT GGA TGG GTT GAG TAC 49 Pro Leu Val Leu Glu Trp Arg Gln Phe Glu Gln Ser Lys Gln Leu Thr
wt    145 CCG CTC GTT TTG GAA TGG AGG CAG TTT GAA CAA AGC AAG CAG CTG ACT
mod       CCT CTT GTT TTG GAA TGG AGG CAA TTC GAG CAA TCT AAG CAA CTT ACT 65 Glu Asn Gly Ala Glu Ser Val Leu Gln Val Phe Arg Glu Ala Lys Ala
wt    193 GAA AAT GGC GCC GAG AGT GTG CTT CAG GTT TTC CGT GAA GCG AAA GCG
mod       GAG AAT GGA GCT GAG AGC GTT CTT CAA GTG TTT AGA GAA GCT AAG GCT 81 Glu Gly Cys Asp Ile Thr Ile Ile Leu Ser ***
wt    241 GAA GGC TGC GAC ATC ACC ATC ATA CTT TCT TAA
mod       GAA GGA TGT GAC ATC ACT ATC ATT CTT TCT TAA
```

Figure 4

SEQUENCE LISTING

```
<160> NUMBER OF SEQ ID NOS: 18

<210> SEQ ID NO 1
<211> LENGTH: 273
<212> TYPE: DNA
<213> ORGANISM: Bacillus amyloliquefaciens

<400> SEQUENCE: 1
atgaaaaaag cagtcattaa cggggaacaa atcagaagta tcagcgacct ccaccagaca      60
ttgaaaaagg agcttgccct tccggaatac tacggtgaaa acctggacgc tttatgggat     120
tgtctgaccg gatgggtcga gtacccgctc gttttggaat ggaggcagtt tgaacaaagc     180
aagcagctga ctgaaaatgg cgccgagagt gtgcttcagg ttttccgtga agcgaaagcg     240
gaaggctgcg acatcaccat catactttct taa                                  273

<210> SEQ ID NO 2
<211> LENGTH: 90
<212> TYPE: PRT
<213> ORGANISM: Bacillus amyloliquefaciens

<400> SEQUENCE: 2

Met Lys Lys Ala Val Ile Asn Gly Glu Gln Ile Arg Ser Ile Ser Asp
1               5                   10                  15

Leu His Gln Thr Leu Lys Lys Glu Leu Ala Leu Pro Glu Tyr Tyr Gly
                20                  25                  30

Glu Asn Leu Asp Ala Leu Trp Asp Cys Leu Thr Gly Trp Val Glu Tyr
            35                  40                  45

Pro Leu Val Leu Glu Trp Arg Gln Phe Glu Gln Ser Lys Gln Leu Thr
        50                  55                  60

Glu Asn Gly Ala Glu Ser Val Leu Gln Val Phe Arg Glu Ala Lys Ala
65                  70                  75                  80

Glu Gly Cys Asp Ile Thr Ile Ile Leu Ser
                85                  90

<210> SEQ ID NO 3
<211> LENGTH: 273
<212> TYPE: DNA
<213> ORGANISM: Artificial sequence
<220> FEATURE:
<223> OTHER INFORMATION: This sequence was artificially generated from a
      wild type barstar gene
```

<400> SEQUENCE: 3

```
atgaagaagg ctgtgatcaa tggagaacaa atcagatcta tctcagacct tcatcaaact    60
ttgaagaagg agcttgctct tcctgagtac tatggtgaga acttggacgc tttgtgggat   120
tgtcttactg gatgggttga gtaccctctt gttttggaat ggaggcaatt cgagcaatct   180
aagcaactta ctgagaatgg agctgagagc gttcttcaag tgtttagaga agctaaggct   240
gaaggatgtg acatcactat cattctttct taa                                273
```

<210> SEQ ID NO 4
<211> LENGTH: 90
<212> TYPE: PRT
<213> ORGANISM: Bacillus amyloliquefaciens

<400> SEQUENCE: 4

```
Met Lys Lys Ala Val Ile Asn Gly Glu Gln Ile Arg Ser Ile Ser Asp
1               5                   10                  15
Leu His Gln Thr Leu Lys Lys Glu Leu Ala Leu Pro Glu Tyr Tyr Gly
            20                  25                  30
Glu Asn Leu Asp Ala Leu Trp Asp Cys Leu Thr Gly Trp Val Glu Tyr
        35                  40                  45
Pro Leu Val Leu Glu Trp Arg Gln Phe Glu Gln Ser Lys Gln Leu Thr
    50                  55                  60
Glu Asn Gly Ala Glu Ser Val Leu Gln Val Phe Arg Glu Ala Lys Ala
65                  70                  75                  80
Glu Gly Cys Asp Ile Thr Ile Ile Leu Ser
                85                  90
```

<210> SEQ ID NO 5
<211> LENGTH: 84
<212> TYPE: DNA
<213> ORGANISM: Artificial Sequence
<220> FEATURE:
<223> OTHER INFORMATION: This oligo was synthetically generated

<400> SEQUENCE: 5

```
atgaagaagg ctgtgatcaa tggagaacaa atcagatcta tctcagacct tcatcaaact    60
ttgaagaagg agcttgctct tcct                                           84
```

<210> SEQ ID NO 6
<211> LENGTH: 85
<212> TYPE: DNA
<213> ORGANISM: Artificial sequence
<220> FEATURE:
<223> OTHER INFORMATION: This oligo was synthetically generated

<400> SEQUENCE: 6

```
aagagggtac tcaacccatc cagtaagaca atcccacaaa gcgtccaagt tctcaccata    60
gtactcagga agagcaagct ccttc                                          85
```

<210> SEQ ID NO 7
<211> LENGTH: 86
<212> TYPE: DNA
<213> ORGANISM: Artificial sequence
<220> FEATURE:
<223> OTHER INFORMATION: This oligo was synthetically generated

<400> SEQUENCE: 7

```
ggatggggttg agtaccctct tgttttggaa tggaggcaat tcgagcaatc taagcaactt    60
actgagaatg gagctgagag cgttct                                         86
```

<210> SEQ ID NO 8
<211> LENGTH: 78
<212> TYPE: DNA
<213> ORGANISM: Artificial sequence
<220> FEATURE:
<223> OTHER INFORMATION: This oligo was synthetically generated

<400> SEQUENCE: 8
ttaagaaaga atgatagtga tgtcacatcc ttcagcctta gcttctctaa acacttgaag      60
aacgctctca gctccatt                                                   78

<210> SEQ ID NO 9
<211> LENGTH: 30
<212> TYPE: DNA
<213> ORGANISM: Artificial sequence
<220> FEATURE:
<223> OTHER INFORMATION: Thsi forward primer was synthetically generated

<400> SEQUENCE: 9
ggctcgagcc accatgaaga aggctgtgat                                       30

<210> SEQ ID NO 10
<211> LENGTH: 29
<212> TYPE: DNA
<213> ORGANISM: Artificial sequence
<220> FEATURE:
<223> OTHER INFORMATION: This reverse primer was synthetically generated

<400> SEQUENCE: 10
ctagtctaga ttaagaaaga atgatagtg                                        29

<210> SEQ ID NO 11
<211> LENGTH: 17
<212> TYPE: DNA
<213> ORGANISM: Artificial sequence
<220> FEATURE:
<223> OTHER INFORMATION: This mutagenic primer was synthetically
      generated

<400> SEQUENCE: 11
tcccacaaag cgtccaa                                                     17

<210> SEQ ID NO 12
<211> LENGTH: 17
<212> TYPE: DNA
<213> ORGANISM: Artificial sequence
<220> FEATURE:
<223> OTHER INFORMATION: This mutagenic primer was synthetically
      generated

<400> SEQUENCE: 12
ttggacgctt tgtggga                                                     17

<210> SEQ ID NO 13
<211> LENGTH: 29
<212> TYPE: DNA
<213> ORGANISM: Artificial sequence
<220> FEATURE:
<223> OTHER INFORMATION: This mutagenic primer was synthetically
      generated

<400> SEQUENCE: 13
caagagggta ctcaacccat ccagtaaga                                        29

```
<210> SEQ ID NO 14
<211> LENGTH: 31
<212> TYPE: DNA
<213> ORGANISM: Artificial sequence
<220> FEATURE:
<223> OTHER INFORMATION: This mutagenic primer was synthetically
      generated

<400> SEQUENCE: 14
ttttggaatg gaggcaattc gagcaatcta a                               31

<210> SEQ ID NO 15
<211> LENGTH: 25
<212> TYPE: DNA
<213> ORGANISM: Artificial sequence
<220> FEATURE:
<223> OTHER INFORMATION: This forward primer for the wild type barstar
      gene was synthetically generated

<400> SEQUENCE: 15
cctcatgaaa aaagcagtca ttaac                                      25

<210> SEQ ID NO 16
<211> LENGTH: 26
<212> TYPE: DNA
<213> ORGANISM: Artificial sequence
<220> FEATURE:
<223> OTHER INFORMATION: This reverse primer for the wild type barstar
      gene was synthetically generated

<400> SEQUENCE: 16
ggtctagatt aagaaagtat gatggt                                     26

<210> SEQ ID NO 17
<211> LENGTH: 24
<212> TYPE: DNA
<213> ORGANISM: Artificial sequence
<220> FEATURE:
<223> OTHER INFORMATION: This forward primer for the modified barstar
      gene was synthetically generated

<400> SEQUENCE: 17
cctcatgaag aaggctgtga tcaa                                       24

<210> SEQ ID NO 18
<211> LENGTH: 29
<212> TYPE: DNA
<213> ORGANISM: Artificial sequence
<220> FEATURE:
<223> OTHER INFORMATION: This reverse primer for the modified barstar
      gene was synthetically generated

<400> SEQUENCE: 18
ctagtctaga ttaagaaaga atgatagtg                                  29
```

METHOD FOR OBTAINING IMPROVED FERTILITY RESTORER LINES FOR TRANSGENIC MALE STERILE CROP PLANTS AND A DNA CONSTRUCT FOR USE IN SAID METHOD

CROSS REFERENCE TO RELATED APPLICATIONS

This application is a National Stage of International Application No. PCT/IN2003/000235, filed Jul. 7, 2003.

REFERENCE TO A SEQUENCE LISTING

A Sequence Listing containing SEQ ID NO: 1-18 is incorporated herein by reference

FIELD OF INVENTION

The present invention relates to a method for obtaining improved fertility restorer lines for male sterile crop plants developed using transgenic approaches for hybrid seed production and a DNA construct for use in said method. In particular, the present invention relates to a method for stable, enhanced and extended temporal expression of a transgene and a method for the development of improved fertility restorer lines for hybrid seed production using molecular approaches in crop plants. The invention relates to the simultaneous use of two different gene sequences encoding the same protein product, one being the naturally occurring wild type sequence and the other sequence generated by modification of the wild type sequence for expression in crop plants by using codon degeneracy to avoid homology between the two sequences at the DNA and mRNA levels, each of the said sequences being placed under independent transcriptional control of different overlapping plant tissue-specific regulatory elements in the same DNA construct.

BACKGROUND OF INVENTION

Genetic transformation of crop plants with heterologous genes is widely recognized as an effective strategy for the introduction of desirable traits such as male sterility/restoration for hybrid seed production, insect resistance, nutritional enhancement, resistance to biotic and abiotic stresses, etc. in crop plants. Expression levels of the transgene(s) are critical for achieving the desired phenotype in transgenic plants. Transgene expression levels can be substantially enhanced by modifications at the transcriptional level (by the use of strong promoters/enhancers) or at the translational level (by modulating parameters viz., codon usage, mRNA stability, etc. associated with coding regions of transgenes). However, the existence of various regulatory mechanisms in plants renders the introduced transgene(s) susceptible to down-regulation which, in many instances, also leads to transgene silencing. Homology based gene silencing (HBGS) has been reported to occur extensively in transgenic plants (Meyer and Saedler 1996, Ann. Rev. Plant Physiol. Plant Mol. Biol. 47:23-48; Vaucheret and Fagard 2001, Trends Genet. 17:29-35) and can occur at the transcriptional (transcriptional gene silencing, TGS) as well as at the post transcriptional levels (post transcriptional gene silencing, PTGS). Such situations can arise when (i) multiple copies of a gene cassette integrate into plants during transformation (van der Krol et al. 1990, Plant Cell 2:291-299), (ii) introduced transgenes are transcribed using homologous promoters (Mol et al. 1989, Plant Mol. Biol. 13:287-294) or (iii) an introduced gene has homology with an endogenous gene in the coding region (Napoli et al. 1990, Plant Cell 2:279-289). Several mechanisms have been suggested to explain the phenomena of HBGS (Matzke and Matzke 1995, Plant Physiol. 107:679-685; Meyer and Saedler 1996, Ann Rev. Plant Physiol Plant Mol. Biol. 47:23-48; Fire 1999, Trends Genet. 15:358-363; Hamilton and Baulcombe 1999, Science 286:950-952; Steimer et al. 2000, Plant Cell 12:1165-1178), the common denominator being that the homology triggers cellular recognition mechanisms that result in silencing of the repeated genes. The present invention relates to a method for enhancing expression levels of transgene(s) while reducing its susceptibility to homology based post transcriptional gene silencing. The strategy of the present invention has been tested by enhancing expression of a restorer gene (barstar) to facilitate effective restoration of male fertility in barnase-containing male sterile transgenic plants for hybrid seed production in crop plants.

The contributions of hybrids towards enhancing crop productivity are well recognized. Increase in crop productivity is due to the phenomenon of heterosis or hybrid vigor in which F1 hybrid plants generated by crosses between two genetically diverse parents exhibit an improved yield than either of the two parents (Banga 1992, In Breeding Oilseed *Brassicas* Eds. Labana K S, Banga S S and Banga S K, Narosa Publishing House, New Delhi; Pradhan et al 1993, Euphytica 69:219-229). Cross pollination is essential for the production of hybrids. In normally self-pollinating crop plants (for example, *Brassica* sp., rice and wheat), one of the parents needs to be male sterile to facilitate cross pollination. In crop plants wherein seeds are the desired economic products, availability of a suitable restorer system in the male parent is essential in order to achieve seed set in the F1 hybrids.

One of the approaches for generation of male sterile/restorer lines for hybrid seed production is the use of cytoplasmic male sterility (CMS)/restorer systems. CMS is a maternally inherited phenomenon, the genetic determinants of which are located in genomes of the cytoplasmic organelles, the mitochondria. Such plants are severely impaired in their ability to produce functional pollen grains. Restorer genes for CMS systems are dominant nuclear genes that suppress male sterile effects of the cytoplasm (i.e., mitochondria). On being incorporated into the male parent, they can be used as restorers of male fertility in F1 hybrids. CMS systems have been widely used in the production of hybrids in sorghum, sunflower, pearl millet and sugar beet. However, their use has been limited in corn, wheat and oilseed *Brassicas* due to linkage of undesirable traits such as increased disease susceptibility, chlorosis, distortion of petals, poor nectary function, etc. with CMS in these systems (McVetty et al 1989, Can J. Plant Sci. 69:915-918; Burns et al 1991, Can. J. Plant Sci. 71:655-661; Williams 1995, Trends Biotech. 13:344-349).

With the advent of recombinant DNA and plant transformation technologies, genetic engineering of male sterility and its restoration have emerged as tangible options for the development of male sterile and restorer lines for hybrid seed production. Male sterility can be artificially induced in plants by introducing a male sterility gene comprising a DNA sequence coding, for example, a cytotoxic product. The cytotoxic product may be a lethal gene under transcriptional control of a promoter which is predominantly active in selective tissue(s) of male reproductive organs in plants. Tapetum, which forms the innermost layers of the anther wall, is one of the most important tissues associated with pollen development. Disruption of tapetal cells by the expression of toxic proteins would therefore impair pollen development leading to male sterile plants. Male sterility was successfully induced in transgenic tobacco and oilseed rape (*Brassica napus*) by targeted expression of a ribonuclease [barnase from *Bacillus amyloliquefaciens* (Hartley 1989, Trends Biochem. Sciences 14:450-454) or Rnase T1 from *Aspergillus oryzae*] in the tapetal tissues using a tapetum-specific promoter (TA29) from tobacco (Mariani et al 1990, Nature 347:737-741).

Presence of a selectable marker gene in male sterility inducing constructs is also essential to facilitate in vitro selection of transformants and for field selection of plants containing the male sterility gene. For example, the bar gene from *Streptomyces hygroscopicus*, conferring resistance to the herbicide, Basta can be used as an in vitro as well as field selectable marker. Use of a strong constitutive promoter to express the marker gene is important for efficient selection of transformants. However, in a study on development of male sterile barnase lines in *Brassica juncea* (Indian mustard) (Jagannath et al 2001, Mol. Breeding 8:11-23), it was found that tissue-specific expression of the barnase gene was deregulated in the presence of a strong constitutive promoter (CaMV35S) that was used to express the herbicide resistance-conferring selectable marker gene (bar) in barnase constructs. Deregulated expression of the cytotoxic barnase gene not only reduced the recovery of transgenic shoots in transformation experiments, but also affected agronomically important traits viz., vegetative morphology, female fertility, seed germination frequencies and inheritance of male sterility in barnase lines rendering them unsuitable for agronomic applications. To circumvent this problem, the above study described a method of using a Spacer DNA fragment to protect tissue-specific expression of the barnase gene which substantially enhanced the recovery of agronomically viable male sterile lines in *Brassica juncea*. Further, all male sterile lines developed in this study were found to be stable over several generations under field conditions in contrast to those developed earlier (Mariani et al 1990, Nature 347:737-741) in which several barnase lines showed breakdown of the male sterile phenotype even under controlled growth conditions (Denis et al 1993, Plant Physiol. 101:1295-1304).

Barnase activity in *B. amyloliquefaciens* is inhibited by a specific inhibitor, barstar, which negates the lethal effects of the ribonuclease by forming a one-to-one complex with the same in the cytoplasm (Hartley and Smeaton 1973, J. Biochem. 248:5624-5626). Expression of the barstar gene under the TA29 tapetum-spaniecific promoter (which is also used for expression of the baniase gene to develop male sterile plants) was shown to restore fertility in barnase lines of *Brassica napus* (Mariani et al 1992, Nature 357:384-387). In the above study, four transgenic barstar lines containing a single copy of the T-DNA insert were crossed to four single-copy male sterile barnase lines in different combinations and resulting F1 hybrids were analyzed for restoration of male fertility in the same. It was found that six of nine crosses performed between barnase and barstar lines produced male fertile progeny while two crosses failed to restore fertility. In one case, partial restoration of fertility was also seen. Inability of some barstar lines to restore fertility was attributed to insufficient levels of the inhibitor protein due to its poor expression. However, the above study was found to be lacking in the analysis of pollen viability in restored plants. Hence, it is not possible to ascertain the extent of fertility restoration in male fertile progeny. This is of particular significance in case of oilseed crops such as *Brassicas* wherein seed set is of paramount importance in achieving full yield potential of the crop.

Plant Genetic Systems have described, in EP 0412911 A1, use of the barstar gene for restoration of fertility in male sterile barnase lines. The above patent describes development of restorer lines in tobacco and oilseed rape using a DNA construct containing three chimeric sequences (i) the barstar gene under transcriptional control of the TA29 tapetum-specific promoter (ii) a selectable marker gene (neo, conferring kanamycin resistance) expressed using a suitable constitutive promoter (pNos) for in vitro selection of transformants and (iii) another selectable marker gene (sfr) expressed using the constitutive Rubisco ssu promoter from *Arabidopsis*. The above patent also describes various breeding strategies which can be used for hybrid seed production using the barnase/barstar system of male sterility and restoration. However, no experimental evidence has been provided for any of these strategies and therefore, the efficacy of the same cannot be conclusively established.

Another strategy for the generation of male sterile and restorer lines using the barnase/barstar system is described in U.S. Pat. No. 5,929,307 wherein the FLP/FRT recombinase system of yeast is used to regulate expression of the barnase and barstar genes. According to one of the embodiments of this invention, a male fertile transgenic plant can be generated by transformation using a vector containing a cytotoxic gene (barnase) and a restorer gene (barstar) wherein the restorer gene is flanked by site-specific (first) recombination sites which are recognized by a specific (first) recombinase. The male sterility and restorer genes are under independent transcriptional control of an anther-specific promoter. Further, the entire functional element composed of the above two genes and their respective promoters is flanked by another set of (second) site-specific recombination sites which are recognized by a specific (second) recombinase. A male sterile plant can be produced by crossing the above male fertile plant with a transgenic plant containing the first site-specific recombinase expressed under a constitutive promoter. Alternatively, the DNA construct used to generate the male fertile plant may also contain the first recombinase expressed under an inducible promoter, in which case, male sterility can be achieved by inducing expression of the first recombinase. Restoration of fertility can be achieved in either case by crossing the male sterile plant with a transgenic plant containing a gene encoding the second recombinase. The invention also describes several other alternative embodiments based on the use of site-specific recombinase systems to generate male sterile lines and for restoration of fertility in the same. However, data presented in the above study only establishes functionality of the yeast FLP/FRT system in maize cells and transformed *Arabidopsis thaliana* plants using various reporter genes. No experimental evidence is presented in support of functionality of the system in induction of male sterility and its restoration based on various strategies described in the same.

Novartis Finance Corporation has described, in U.S. Pat. No. 6,147,282, another strategy for controlling plant fertility based on chemical control of gene expression in plants. According to this strategy, chemical ligands can be used to activate receptor polypeptides (for example, the Ecdysone and USP receptors containing ligand-binding and DNA-binding domains) which, in turn, induce expression of a target gene (barnase or boustar) expressed using a promoter containing suitable receptor binding elements. According to the patent, the above strategy could be used for induction of male sterility as well as its restoration. Male sterile transgenic plants can be generated using a DNA construct containing: (i) the barnase gene expressed under suitable anther-specific promoters (for example, TA29) (ii) the receptor expression cassettes (encoding the Ecdysone and USP receptor polypeptides) under regulatory control of the same anther specific promoter or from constitutive promoters (for example, maize ubiquitin, 35S or rice actin) and (iii) a target expression cassette having a 5' regulatory element (containing the appropriate response element sequence and core promoter elements)

linked to the barstar gene. In order to restore fertility, a suitable chemical ligand (for example, RH5992) can be sprayed on the male sterile transgenic plants. This would induce heterodimerization of the USP and Ecdysone receptor polypeptides resulting in the activation of the 5' regulatory sequence of the target (barstar) expression cassette and production of barstar protein which would inhibit barnase and restore male fertility. The functionality of the above strategy was demonstrated using the luciferase reporter gene as the target polypeptide. Expression of luciferase protein was reported to increase approximately 2-4 folds upon induction over that observed in the absence of the chemical ligand. However, in the absence of corresponding data on expression of barstar protein for restoration of male fertility and in light of published literature on problems associated with development of male sterile lines due to deregulated expression of cytotoxic gene(s) (see above), efficiency of the above strategy in achieving the desired fertility status in crop plants needs to be established. Moreover, this strategy requires exogenous application of chemicals to induce the desired fertility status. For crop plants grown on a large acreage, this might not only be economically unsound, but the duration, time and amount of the desired ligand to be sprayed on standing crops would also be highly variable leading to inconsistency in production parameters.

Transgene expression levels can be enhanced by modification of the coding sequence to introduce preferentially used codons (for improved mRNA translation) and to ensure removal of potential deleterious signals which might inhibit transgene expression. Modified genes have been shown to improve transgene expression levels in heterologous systems including bacteria, plants and animal cell lines (Wosnick et al 1989, Gene 76:153-160; Adams et al 1988, Nucl. Acids Res. 16:4287-4298; Perlak et al 1991, PNAS-USA 88:3324-3328; Koziel et al 1993, BioTechnology 11:194-200; Pang et al 1996, Plant Physiol. 105:473-482). Common factors which have been taken into consideration for designing modified genes for improved expression in plant systems include codon usage, mRNA instability sequences (for example, polyadenylation signals), GC-content and plant intron consensus sequences. The cry genes of *Bacillus thuringiensis*, encoding the insecticidal-δ-endotoxins, are some of the best representative examples of bacterial genes modified for enhanced expression in transgenic plants (Perlak et al 1991, PNAS-USA 88:3324-3328; Adang et al 1993, Plant Mol. Biol. 21:1131-1145; Fujimoto et al 1993, BioTechnology 11:1151-1155; Strizhov et al 1996, PNAS-USA 93:15012-15017; Iannaocone et al 1997, Plant Mol. Biol. 34:485-496). However, in a study by Rouwendal et al (1997) on the wild type and modified versions of the Green Fluorescent Protein (GFP) gene, no enhancement in expression levels could be achieved using modified transgenes in comparison to that obtained using the wild type sequence (Rouwendal et al 1997, Plant Mol. Biol. 33:989-999). In another study on the luciferase gene, it was reported that while the modified gene sequence may enhance expression of the transgene in one plant system, it may not do so in others (Lonsdale et al 1998, Plant Cell Rep. 17:396-399).

Plant Genetic Systems, in WO9810081, has described modification of the barstar gene sequence for enhanced expression in plant cells. According to the invention, the modified barstar DNA could be used for the development of efficient restorer lines which are capable of restoring fertility to a variety of male sterile lines (with varying levels of barnase expression) and are particularly useful for producing restorer lines in cereals, especially in corn, rice and wheat. The improved barstar gene sequence described in this invention encodes a barstar protein with an altered N-terminal amino acid sequence that starts with Methionine followed by "X" amino acid wherein "X" is either Alanine, Valine, Glycine, Aspartic acid or Glutamic acid, preferably Alanine encoded by a GCC codon. The preference for these amino acids is because, all available codons of these amino acids begin with a G nucleotide and being the second amino acid in the modified barstar gene sequence, it would provide an optimal translation initiation context at position +4. The modified barstar gene of the invention has an amino acid sequence which is "Met-Ala-Lys" while the wild type protein begins with "Met-Lys" at the N-terminal end. Other criteria used for designing the modified barstar gene sequence (also referred to as "synthetic barstar DNA") of the above invention and incorporated therein were:

(a) Codon usage: The modified sequence has a codon usage that is optimized for oilseed rape, cotton, maize, rice and wheat, preferably for oilseed rape (*Brassica napus*), maize and rice. For the purpose of this invention, the overall codon frequencies for various plant species described by Ikemura were used (Ikemura 1993, In "Plant Molecular Biology Labfax", Croy ed., Bios Scientific Publishers Ltd., pp. 37-48). According to this invention, the preferred codon selected for incorporation in the modified barstar sequence is one, which, in each of more than N/2 plant species (N=No. of plant species for which codon usage patterns are taken into account for design of the modified sequence) has an overall frequency that is at least twice the overall frequency of the least used codon and/or more than half of the overall frequency of the most used codon (b) AT-content: A and T nucleotides constitute less than 40% of the sequence composition. This was primarily done to reduce the probability of introducing polyadenylation signals and intron recognition sequences which are known to destabilize transgene expression and can occur with a greater probability in AT-rich sequences. The synthetic barstar sequence of the invention has an AT-content of 38.4% while the wild type sequence is characterized by an AT-content of 51.6%.

(c) CG and CNG sequences: CG and CNG sequences have been shown to be associated with DNA methylation and gene silencing in plants. The modified sequence should not contain more than 7% CG dinucleotides and/or no more than 9.5% of CNG trinucleotides. The synthetic barstar DNA of the above invention contains 16 CG dinucleotides and 24 CNG trinucleotides while the wild type sequence has 14 CGs and 22 CNGs.

(d) The modified sequence is further characterized by having no more than 7, preferably no more than 5, particularly no more than 3 tetranucleotides consisting of only one kind of nucleotide and having no more than 2, preferably no more than 1 pentanucleotide consisting of only one kind of nucleotide. The synthetic barstar DNA of the invention contains one CCCCC and one GGGG stretch.

The improved barstar gene was deployed for the development of restorer lines in rice, corn and oilseed rape. In transgenic rice plants generated using the wild type and synthetic barstar genes under regulatory control of appropriate male tissue-specific promoters, it was found that the synthetic gene produced more barstar protein with the amount of barstar protein being proportional to the amount of barstar mRNA present. Crosses between male sterile barnase lines and restorer barstar plants showed that restoration capabilities were directly comparable with the amount of barstar protein produced. Plants producing 50 ng or more barstar/mg of extracted protein functioned as efficient restorer lines while plants producing between 4-10 ng barstar/mg of extracted protein could only induce partial restoration of male fertility. While plants with barstar expression levels >50 ng/mg of total protein could be obtained with the synthetic barstar gene, none of the plants generated using the wild type gene gave comparable expression levels. Similar studies were performed on transgenic corn plants. One male sterile line (designated MS3), which, according to the inventors, was a considerably difficult line to restore (data not shown), was selected for testing restoration capabilities of restorer lines generated using the wild type and synthetic barstar genes. Crosses between the male sterile MS3 line and seven wild type barstar restorer lines did not identify any suitable restorer, with maximally 75% of anthers producing viable pollen. On testing the MS3 line with restorer lines generated using the synthetic barstar sequence, it was found that four out of six lines tested were able to achieve complete restoration of male fertility thereby demonstrating that restorer lines generated using the synthetic barstar gene have a significantly better restoration capacity. The inventors further report that the amount of barstar protein in two restorer plants developed using the synthetic barstar DNA was much higher (210 and 100 ng barstar/mg total protein) than that observed in one wild type barstar plant (20 ng barstar/mg total protein). Transgenic plants were also generated in oilseed rape using the wild type and synthetic barstar genes. Analysis of activity of the wild type and synthetic barstar proteins revealed that activity of the improved barstar protein was at least equivalent to that of its wild type counterpart. However, no data were reported on restoration capabilities of these barstar lines. It is also important to note here that the above studies are lacking in data on copy numbers of the integrated transgene for the experimental lines used. Therefore, it is probable that position effects and varying copy numbers of the barstar gene may be influencing barstar expression levels in independent transgenic plants. Moreover, in the absence of data on pollen viability in restored plants, extent of restoration cannot be determined accurately.

Several strategies have been developed for generation of restorer lines for hybrid seed production. One of these studies has also addressed the issue of expression level of the restorer gene product and has prescribed the design and use of synthetic DNA sequences for enhanced expression in heterologous systems to facilitate effective restoration. However, none of the described strategies highlight the extent of restoration with reference to pollen viability which is a critical parameter for determining the efficacy of any restoration strategy. Additionally, most strategies rely on the use of several superfluous genes, promoters and other DNA sequences, the presence of which is highly undesirable in transgenic crop systems.

The present invention describes a method for enhancing expression levels of transgene(s) while reducing its susceptibility to homology based post transcriptional gene silencing. It further describes a method for achieving stable, enhanced and extended temporal expression of a restorer gene product based on the simultaneous use of two different restorer gene sequences encoding the same protein product in the same DNA construct. One of the said sequences is modified for expression in dicotyledonous crop plants using codon degeneracy to avoid homology between the two sequences at the DNA and mRNA levels and the other is the naturally occurring wild type sequence, each of which is placed under independent transcriptional control of regulatory elements with overlapping expression patterns in male reproductive tissues. In addition to enhancing restorer gene expression, simultaneous use of two different DNA sequences (which would transcribe two different RNA molecules) in the same DNA construct confers the added advantage of avoiding homology based post transcriptional gene silencing. The method described in the present invention can also be applied with suitable modifications to other molecular methods based on the expression of a cytotoxic gene and its corresponding inhibitor for the development of male sterile and restorer lines, respectively.

OBJECTS OF THE INVENTION

The main object of the invention is to provide a novel method for enhancing expression levels of transgene(s) with reduced susceptibility to homology based post transcriptional gene silencing by the simultaneous use of two different DNA sequences encoding the same protein product.

Another object of the invention is to provide a method for achieving stable, enhanced and extended temporal expression of a restorer gene product in male reproductive tissues for the development of improved restorer lines in crop plants for hybrid seed production.

Yet another object is to provide a modified sequence of a restorer gene designed for expression in dicotyledonous crop plants.

A further object is to provide a DNA construct containing two different coding sequences of a restorer gene—one modified for expression in dicotyledonous crop plants using codon degeneracy to avoid homology between the two sequences at the DNA and mRNA levels and another which is the naturally occurring wild type sequence—each under independent transcriptional control of regulatory elements with overlapping expression patterns in male reproductive tissues, the protein product generated using the wild type and modified sequences remaining identical.

Another object is to develop a DNA construct that would enhance expression of the restorer gene product while providing protection against post-transcriptional gene silencing.

Yet another object is to develop improved restorer lines using the DNA construct of the invention.

Still another object is to develop methods for the identification of improved restorer lines generated using the DNA construct of the invention.

SUMMARY OF INVENTION

The present invention relates to a method for enhancing expression levels of transgene(s) while reducing its susceptibility to homology based post transcriptional gene silencing. The invention provides a novel method for achieving stable, enhanced and extended temporal expression of a restorer gene product in male reproductive tissues for the development of improved fertility restorer lines in crop plants for hybrid seed production. The invention also provides a modified restorer gene sequence designed for expression in dicotyledonous crop plants using codon degeneracy to avoid homology between the modified sequence and the wild type sequence at the DNA and mRNA levels. Further, the invention provides a DNA construct comprising: (i) a first transcription unit containing the wild type sequence of a restorer gene under transcriptional control of a suitable first tapetum-specific promoter (which is used to express the male sterility gene in corresponding male sterile plants) and fused to a suitable transcription termination signal including a polyadenylation signal, (ii) a second transcription unit comprising a modified sequence of the restorer gene, designed for expression in dicotyledonous crop plants, under transcriptional control of a second tapetum-specific promoter and fused to a suitable transcription termination signal including a polyadenylation signal and (iii) a third transcription unit comprising a selectable marker gene under transcriptional control of a strong constitutive promoter and fused to a suitable transcription termination signal including a polyadenylation signal. The second tapetum-specific promoter in the DNA construct of the invention is selected such that the first and second tapetum-specific promoters have overlapping expression profiles. Further, the invention describes methods for the development and identification of improved restorer lines using the said DNA construct.

DETAILED DESCRIPTION OF INVENTION

The present invention relates to a method for enhancing expression levels of transgene(s) while reducing its susceptibility to homology based post transcriptional gene silencing. It further describes a method for achieving stable, enhanced and extended temporal expression of a restorer gene product in male reproductive tissues and a method for the development of improved fertility restorer lines in crop plants for hybrid seed production. The method of the present invention is based on the simultaneous use of two different restorer gene sequences—one being the naturally occurring wild type sequence and the other sequence generated by modification of the wild type sequence for expression in dicotyledonous crop plants by using codon degeneracy to avoid homology between the modified sequence and the wild type sequence at the DNA and mRNA levels—each of the said sequences being placed under independent transcriptional control of different overlapping plant tissue-specific regulatory elements in the same DNA construct. Accordingly, the invention provides a DNA construct comprising:

(i) a first transcription unit comprising the wild type sequence of a restorer gene under transcriptional control of a suitable first tissue-specific promoter (which is used to express the male sterility gene in corresponding male sterile plants) and fused to a suitable transcription termination signal, including a polyadenylation signal, (ii) a second transcription unit comprising a modified sequence of the restorer gene, designed in the present study for expression in dicotyledonous crop plants, under transcriptional control of a second tissue-specific promoter and fused to a suitable transcription termination signal including a polyadenylation signal, and (iii) a third transcription unit comprising a selectable marker gene under transcriptional control of a strong constitutive promoter and fused to a suitable transcription termination signal including a polyadenylation signal.

In an embodiment, the restorer genes that can be used in the DNA construct of the invention could be any coding sequence which can inhibit or negate the cytotoxic effects of another DNA sequence or its encoded product thereby protecting the cell from lethal effects of the cytotoxic gene. Instances of such restorer genes include barstar (inhibitor of the ribonuclease, barnase) or protease inhibitors (which neutralize the activity of proteases such as papain). In a preferred embodiment, the restorer gene used in the present invention is the barstar gene from *Bacillus amyloliquefaciens* which functions as an intracellular inhibitor of barnase. In a preferred embodiment of the invention, two different versions of the barstar gene are used in independent transcription units for stable, enhanced and extended temporal expression of the restorer gene product. One of the sequences is represented by the wild-type gene and the other is a modified sequence designed for expression in dicotyledonous crop plants.

The modified sequence of the restorer gene (barstar) was designed based on parameters known to influence transgene expression in heterologous systems. Critical parameters taken into consideration for designing the modified sequence and changes incorporated therein are described hereunder.

(1) Codon Usage:

Codon usage patterns have been well characterized for several organisms viz. *E. coli, Bacillus, Agrobacterium*, yeast, *Drosophila*, man and higher plants. Codon usage variations have a significant impact on gene expression in heterologous systems. Hence, while designing genes for enhanced expression, it is important to replace codons that are least favored in the target system with appropriate synonymous codons to facilitate improved translatability of mRNA. Based on published data on codon usage patterns for various organisms (Murray et al 1989, Nucl. Acids Res. 17:477-498; Wada et al 1992, Nucl. Acids Res. 20 Supplement: 2111-2118; Nakamura et al 1997, Nucl. Acids Res. 25:244-245), a codon usage table for dicotyledonous plants was developed to design a modified sequence of the barstar gene (Table 1). For clarity and convenience in selection of codons for incorporation in the modified sequence, all codons for each amino acid were categorized (wherever possible) into 3 classes:

1. Optimal codons: that have maximum usage in the system.

2. Sub-optimal codons: with an intermediate usage between the Optimal and Rare codons 3. Rare codons: with a usage less than 50% of the usage of the Optimal codons.

TABLE 1

Codon usage table for dicot plants

| Amino acid | Optimal codon(s) | Sub-optimal codon(s) | Rare codon(s) |
|---|---|---|---|
| Arginine | AGA<br>AGG | CGT | CGC<br>CGA<br>CGG |
| Leucine | CTT<br>TTG | CTC | TTA<br>CTA<br>CTG |
| Serine | TCT | TCC<br>TCA<br>AGC<br>AGT | TCG |
| Threonine | ACT | ACC<br>ACA | ACG |
| Proline | CCT<br>CCA | — | CCC<br>CCG |
| Alanine | GCT | GCA<br>GCC | GCG |
| Glycine | GGA<br>GGT | — | GGG<br>GGC |
| Valine | GTT | GTG | GTC<br>GTA |
| Lysine | AAG | — | AAA |
| Asparagine | AAC | AAT | — |
| Glutamine | CAA | CAG | — |
| Histidine | CAT | CAC | — |
| Glutamic acid | GAG<br>GAA | — | — |

TABLE 1-continued

Codon usage table for dicot plants

| Amino acid | Optimal codon(s) | Sub-optimal codon(s) | Rare codon(s) |
|---|---|---|---|
| Aspartic acid | GAT GAC | — | — |
| Tyrosine | TAC TAT | — | — |
| Cystine | TGT TGC | — | — |
| Phenyl alanine | TTC TTT | — | — |
| Isoleucine | ATT | ATC | ATA |
| Methionine | ATG | n.a. | n.a. |
| Tryptophan | TGG | n.a. | n.a. | n.a.: not applicable

In an embodiment of the present invention, forty seven codons (of a total of 91 codons) from the wild type barstar gene were replaced by preferentially used codons in the modified sequence. On the basis of the three-tier classification of codons for dicot systems described above, the wild type gene was found to have a codon usage comprising 50 optimal codons, 25 sub-optimal codons and 15 rare codons (excluding the termination codon). The modified sequence on the other hand, is composed of 78 optimal codons and 12 sub-optimal codons with complete exclusion of rare codons. Retention of 12 sub-optimal codons was primarily due to consideration of other parameters (as described below) for designing a modified gene sequence.

(2) Potential mRNA Instability Sequences and Plant Poly(A) Signals:

An important mechanism regulating gene expression operates at the level of mRNA turnover. Several sequences governing instability of mRNAs have been studied and characterized. For example: the 40 bp DST sequences found downstream of the coding region in Small Auxin Up RNA (SAUR) transcripts of several plants (McClure et al 1989, Plant Cell 1:229-239) and the AUUUA repeat motif in the 3' untranslated regions (ULTR) of several mammalian (Peltz et al 1991, In Critical Review, Eukaryotic Gene Expression, Eds. Stein J S, Stein J L and Lian J B, CRC Press) and plant mRNAs. AT-richness has also been implicated in modulating mRNA stability in plants. However it has been shown that the effect of AT-rich sequences on mRNA stability is sequence-specific (consisting of ATTTA repeats) and not simply due to high AT-content (Ohme-Takagi et al 1993, PNAS-USA 90:11811-11815).

Sequences favoring mRNA stability have not yet been well characterized with the exception of the poly(A) tail. Poly(A)-binding proteins (PABPs) have been implicated in governing mRNA stability. Available data suggest that plant PABPs may play an important role in organ-specific, post-transcriptional control of gene expression by influencing mRNA stability. The most widely used Plant Polyadenylation Signal Sequence (PPSS) is AATAAT although several others, a representation of which is given below, have also been proposed to be functional at low frequencies (Dean et al 1986, Nucl. Acids Res. 14:2229-2240):

$A_{15} \ A_9 \ T_6 \ A_8 \ A_{13} \ T_8$ $T_6 \ A_5 \ C_6 \ T_2 \ A_7$ $G_3 \ T_1$ $C_1$

These consensus sequences were derived from a study of 15 sequences representing cDNA clones of rbcs and cab genes from petunia and bronze genes from maize. Numbers in subscripts indicate the relative preference for a nucleotide at a particular position in the poly(A) signal sequence of the 15 sequences analyzed.

Presence of such signal sequences in the coding sequence of a gene might lead to premature termination of mRNA synthesis leading to unstable expression of the target gene. Therefore, it is advisable to remove such putative mRNA instability sequences as well as PPSS sequences from the coding regions of transgenes to prevent any adverse effects on transcript stability/expression. Consensus sequences for the above types of signals were absent in the wild type sequence and were also not created during design of the modified gene sequence.

(3) Plant Intron Consensus Sequences:

Plant introns are characterized by the presence of 5' and 3' splice sites and a branch point, all of which have well-characterized consensus sequences (Wiebauer et al 1988, Mol. Cell. Biol. 8:2042-2051; Goodall and Filipowicz 1989, Cell 58:473-483; Schuler 1998, In A Look Beyond Transcription: Mechanisms Determining mRNA Stability and Translation in Plants, Bailey-Serres J and Gallie D R, Eds. American Society of Plant Physiologists; see Table below).

| Motif | Sequence |
|---|---|
| 5' Splice site | AG/<u>GTAAGT</u> |
| Branch point | CTN<u>AN</u><br>TTN<u>AN</u> |
| 3' Splice site | GC<u>AG</u>/G |

Underlined nucleotides represent bases that are highly conserved in all plant introns. Abbreviations: A: Adenine, T: Thymine, G: Guanine, C: Cytosine, N: A, T, G or C, Y: Cytosine or Thymine, R: Adenine or Guanine.

In order to prevent any undesirable post-transcriptional processing of the transgene mRNA, it is necessary to remove potential 5'/3' splice sites and branch points from the coding region of a transgene. The wild type sequence of the barstar gene carries three branch point consensus sequences and one 3' splice site consensus sequence which were eliminated from the modified sequence during gene design.

(4) Methylation-Prone Sequences:

Transgene silencing in plants has almost always been found to be associated with methylation of the transgene sequences at 'CG' and 'CNG' residues and involves transcriptional inactivation (which is meiotically heritable) as well as post-transcriptional processes (which are reset after meiosis). Methylation of both upstream regulatory sequences (Matzke et al 1989, EMBO J. 8:643-649; Linn et al 1990, Mol. Gen. Genet. 222:329-336; Matzke and Matzke 1991, Plant Mol. Biol. 16:821-830; Kilby et al 1992, Plant Mol. Biol. 20:103-112; Meyer et al 1993, Plant J. 4:89-100; Matzke et al 1994, Mol. Gene Genet. 244:219-229; Meyer and Heidmann 1994, Mol. Gen. Genet. 243:390-399) as well as coding regions of transgenes (Meyer and Heidmann 1994, Mol. Gen. Genet. 243:390-399; Meyer et al 1993, Plant J. 4:89-100) has been reported in several transgenic plant systems. To minimize the influence of 'CG' and 'CNG' residues in mediating transgene silencing, it is advisable to remove them from the coding regions of transgenes by using codon degeneracy. There are, however, several codons which, although inherently lack a 'CG' or a 'CNG', can introduce such sites when the amino acids encoded by such codons occur in tandem in the protein sequence. For example: ala-ala, ala-asp, pro-ala, ala-gly, ala-glu, thr-gly, pro-gly, ala-val, pro-glu, thr-glu, thr-val, pro-asp, thr-asp and pro-val. In such situations, it is not possible to remove CG/CNG sites using codon degeneracy. The number of CGs and CNGs has been reduced in the modified barstar gene sequence to 3 and 8 respectively from the corresponding figures of 14 and 22 in the wild type sequence. Complete removal of CGs and CNGs from the modified sequence has not been possible due to the tandem arrangement of some amino acids as described above.

(5) GC-Content:

Analysis of gene sequences from plant systems has revealed that plant genes have a characteristic GC-content which is seen to vary between monocot and dicot species. While monocot genes have an average GC-content of 60-70%, dicot genes are characterized by a GC-content of 42-46% (Salinas et al 1988, Nucl. Acids Res. 16:4269-4285). GC-content also plays an important role in influencing DNA methylation. Genes located in a GC-rich region are characterized by relatively higher levels of methylation as compared to those in AT-rich regions. Significant variations in GC-content between the transgene and the endogenous genes at the site of integration may render the former susceptible to methylation-induced silencing. Hence, while designing genes for enhanced expression in a heterologous system, it is advisable to maintain GC-content of the transgene around the average prescribed GC-content of the expression system.

The wild-type transgene sequence was also analyzed for the presence of AT- and GC-rich sequences and those greater than 4 nucleotides in length were removed from the modified sequence (without compromising on other critical parameters) during gene design. This parameter assumes significance because long stretches of AT/GC might not only interfere with design of suitable oligos for gene synthesis but also influence mRNA processing (stability) and GC-content of the transgene. Reduction in the number of such sequences would serve to ensure a more equitable distribution of various nucleotides over the gene sequence rendering it more homogeneous in its GC-content.

Following incorporation of all the aforementioned modifications, the GC-content of the modified sequence was 42.1% while that of the wild-type sequence was 48.4%. Both the wild type and modified genes have a GC-content that falls within the average range of %-GC for dicot genes (42-46%).

(6) Consensus Translational Start Site

The context of the ATG codon of a gene is known to play a significant role in influencing translation initiation (Kozak 1986, Cell 44:283-292). A consensus sequence for this region has been arrived at on the basis of an extensive study of several plant genes by Kozak (Kozak 1984, Nucl. Acids Res. 12:857-872) and Joshi (Joshi 1987, Nucl. Acids Res. 15:6643-6653). The consensus sequence reported by Kozak (1984) has been incorporated (with a minor change) in the context of the first ATG codon of the modified barstar gene as shown below.

```
Context of ATG codon of        5'-CCACC ATG AAG-3'
modified barstar gene                  Met Lys Kozak's consensus for plant    5'-CCACC ATG G-3'
genes                                  Met
```

This change became necessary in view of the non-availability of a codon beginning with 'G' for Lysine.

Alterations effected in the modified barstar gene sequence are summarized in Table 2 below.

TABLE 2

Summary of modifications made in the modified barstar gene sequence vis-à-vis the wild-type sequence.

| S. No. | Parameter | Wild-type barstar gene | Modified barstar gene |
|---|---|---|---|
| 1. | Potential poly(A) signals | 0 | 0 |
| 2. | mRNA instability sequence [(ATTTA)$_n$] | 0 | 0 |
| 3. | Methylation-prone sequences | | |
| | CG | 14 | 3 |
| | CNG | 22 | 8 |
| 4. | Plant intron consensus sequences (*) | | |
| | a) Branch point sequences | | |
| | YNYYRAY | 1 | 0 |
| | CYRAY | 2 | 0 |
| | b) 5' splice site (AAGGTAAGT) | 0 | 0 |
| | c) 3' splice site (TNYAGG) | 1 | 0 |
| 5. | AT-stretches (WWWW) | 17 | 5 |
| 6. | GC-stretches (SSSS) | 12 | 0 |
| 7. | GC-content | 48.4% | 42.1% |

*consensus sequences available till 1996 have been taken into consideration for gene design in the present study; W: Adenine or Thymine; S: Guanine or Cytosine.

In an embodiment of the invention, the wild type and modified sequences of the barstar gene are expressed in a tissue-specific manner using tapetum-specific promoters which have overlapping expression profiles in the target tissues. Tissue-specific promoters are characterized by definite temporal and spatial expression patterns during plant growth and development. Several such promoters have been characterized from plant systems. A few examples include anther-specific promoters such as TA29, A9, tap1, bcp1 or seed specific promoters such as napin or promoters such as AP3 which express in a relatively wider manner in floral tissues. The tissue-specific promoters in the DNA construct of the present invention are selected such that the first and second tissue-specific promoters have overlapping expression profiles. In a preferred embodiment, the first tissue-specific promoter used to express the wild type barstar sequence is the tapetum-specific promoter, TA29 (Seurinck et al 1990, Nucl. Acids Res. 18:3403), while the second tissue-specific promoter used to express the modified sequence of barstar gene is another tapetum-specific promoter, A9 (Paul et al 1992, Plant Mol. Biol. 19:611-622).

A selectable marker gene encodes an RNA or protein which, when expressed in the cells of a plant, gives the cells expressing the gene a selective advantage over cells lacking the same. In an embodiment, the marker gene is selected from the group of herbicide resistance-conferring genes such as bar, tfdA, ALS; antibiotic resistance-conferring genes such as nptII, hpt, aadA, etc. In a preferred embodiment of the invention, the selectable marker gene used for in vitro and in vivo selection of transformed tissues is the herbicide resistance conferring gene, bar, from *Streptomyces hygroscopicus*. In another preferred embodiment of the invention, the marker gene used for in vitro selection is the hpt gene conferring resistance to hygromycin.

In an embodiment, the promoter used for driving the expression of the bar gene is the CaMV35S promoter with a duplicated enhancer (henceforth referred to as CaMV35Sde) which is a known strong constitutive promoter. The duplication of the enhancer region (−343 to −90) has been shown to enhance expression of the CaMV 35S promoter by 10-fold (Kay et al 1987, Science 236:1299-1304). In another embodiment, the promoter used for expression of the hpt gene is the CaMV35S promoter with a single enhancer.

The transcription unit of the selectable marker gene (bar or hpt) is placed towards the Left Border of T-DNA (in an appropriate binary vector) to ensure complete transfer of all components located between the T-DNA borders during *Agrobacterium*-mediated genetic transformation.

The method outlined in the present invention for enhanced expression of a transgene with reduced susceptibility to homology based gene silencing is based on the simultaneous use of two different sequence versions (wild type and modified) of a restorer gene, both of which encode identical protein products and are placed under independent transcriptional control of two different regulatory elements having overlapping expression profiles. The efficacy of the above method in developing efficient restorer lines by enhancing expression of the restorer gene product can be tested either by crossing transgenic barstar lines generated using constructs described in the present invention with male sterile barnase lines or by retransforming barnase-containing male sterile plants with barstar constructs. In the latter approach, to facilitate efficient selection of transformants containing both the male sterility and restorer genes, the marker gene used in the DNA construct of the present invention could be different from that present in the male sterile transgenic plant(s). For example, male sterile plants containing the bar gene as a selection marker can be transformed with restorer DNA constructs containing the hpt gene for selection of transformants. A similar approach can be used for other combinations of marker genes used for generation of male sterile and restorer plants. The frequency of male fertile transformants among transgenic plants containing both the marker genes (i.e., both the barnase and barstar genes) would reflect the efficacy of the strategy in development of efficient restorers for male sterile lines in crop plants.

The efficacy of the aforementioned strategy was tested by transforming a stable, male sterile barnase line (bn 3.6; containing the bar gene as a selectable marker; Jagannath et al 2001, Mol. Breeding 8:11-23) with a DNA construct containing the wild type and modified sequences of the barstar gene under transcriptional control of the TA29 and A9 promoters respectively and the hpt gene under transcriptional control of the CaMV35S single enhancer promoter as a selectable marker. As appropriate controls, the male sterile plant was also transformed with DNA constructs containing a single copy of the wild type barstar gene under transcriptional control of either the TA29 or A9 promoter. Transformants containing both the barnase and barstar genes were obtained by sequential selection on selective media containing hygromycin (from barstar T-DNA) and Basta (Agrevo; from barnase T-DNA). Transgenic plants were transplanted in a nethouse under field conditions during the growing season (October-April) and analysed for their male fertility/sterility phenotype.

Use of the barstar gene as a restorer of male fertility requires that it is expressed equally or to a greater extent than the barnase gene. Transgenic plants wherein barstar expression levels are sufficient to counter the lethal effects of barnase would be male fertile. Since barnase levels are identical in all transformation experiments with both control and test DNA constructs, any variation in the frequency of fertile (i.e., restored) plants would be primarily due to differences in barstar levels in the same.

Restoration of male fertility in transformed plants containing both the barnase and barstar genes was analyzed on the basis of pollen formation, pollen viability and formation of selfed seeds and correlated with copy number of the barstar gene cassette in the same. Results on the frequency of fertile (restored) plants obtained from transformation of the barnase line with various barstar constructs are summarized in Table 3 below.

TABLE 3

Frequency of fertility restoration in bn 3.6 using barstar constructs

| Construct Code | Construct | No. of Basta$^R$-Hyg$^R$ plants analysed in field | Fertility status F | S | SF | Percent of restored plants |
|---|---|---|---|---|---|---|
| A | A9-bs(fm) :: TA29-bs(wt) | 88 | 79 | 8 | 1 | 89.8 |
| B | TA29-bs(wt) | 64 | 42 | 15 | 7 | 65.6 |
| C | A9-bs(wt) | 47 | 6 | 40 | 1 | 12.7 |
| D | A9-bs(fm) | 46 | 5 | 38 | 4 | 10.8 |

F: Fertile;
S: Sterile;
SF: Semi-fertile;
bs(wt): wild type barstar gene;
bs(mod): modified barstar gene The above results indicate that restoration of fertility using constructs containing a single copy of the wild type or modified barstar gene (Constructs C, D) under transcriptional control of the A9 promoter was very low (12.7% and 10.8%; Table 3). The frequency of obtaining fertile plants with the TA29-bs(wt) construct (Construct B) was much higher (65.6%). This difference in restoration capability can be attributed to the fact that the barnase gene in the male sterile parent is under transcriptional control of the TA29 promoter. Therefore, in such plants transformed with the TA29-bs(wt) construct, both the barnase and barstar genes would have a similar temporal expression profile leading to simultaneous production of both the barnase and barstar proteins. Expression from the A9 promoter, on the other hand, ends earlier than that of the TA29 promoter. Therefore, no barstar protein would be available to inhibit the lethal effects of barnase during later stages of TA29-barnase expression and plants would therefore be male sterile.

On using construct A [A9-bs(fm)::TA29-bs(wt)], the frequency of fertile plants registered a substantial increase to 89.8% indicating that barstar levels are significantly higher as compared to the earlier (control) constructs. In fertile plants derived using construct A, the presence of two independent transcriptional units for the barstar gene leads to the formation of more barstar mRNA and hence more barstar protein. Since the tapetum-specific promoters used to transcribe the barstar gene have overlapping expression profiles, accumulation of barstar protein in tapetal tissues begins earlier (from the A9 promoter) than barnase (which is under transcriptional control of the TA29 promoter) and continues during the entire period when barnase is expressed (from the TA29-barstar cassette). Extended expression of the barstar gene therefore builds up a reservoir of the inhibitor protein which ensures effective inhibition of barnase.

The occurrence of a few fertile plants among transformants generated using Constructs C and D could be due to position effect-mediated enhancement of barstar gene expression and these were not taken further for subsequent analysis. Similarly, the occurrence of semi-fertile and male sterile plants could be attributed to position effect-mediated inhibition of barstar expression. It is nevertheless also important to note that the occurrence of semi fertile plants among transformants generated using Construct A is significantly lower than those obtained with Construct B indicating the greater efficiency of Construct A in generation of male fertile plants.

To determine the extent of fertility restoration, male fertile (restored) plants obtained using Constructs A and B were analyzed for their pollen viability. Fertile, restored plants derived from each of the above constructs were classified into the following three categories on the basis of their pollen viability: <50%, 50-90%, >90%. In case of efficient restoration, pollen viability in restored events is expected in the range of 90-100% similar to that observed in untransformed control plants or in transgenic plants lacking the barnase gene. Pollen viability data of transformed male fertile (restored) plants is summarized in Table 4 below.

TABLE 4

Pollen viability of male fertile, restored events

| Construct code | Construct | No. of fertile plants analysed | No. of plants with pollen viability | | | % of plants with PV > 90% |
|---|---|---|---|---|---|---|
| | | | <50% | 50-90% | >90% | |
| A | A9-bs(fm) :: TA29-bs(wt) | 79 | 3 | 24 | 52 | 65% |
| B | TA29 :: bs(wt) | 42 | 1 | 21 | 20 | 47.6% |

PV: pollen viability

From the above data, it is clear that fertile (restored) plants with pollen viability >90% were obtained at a greater frequency using Construct A (65%) as compared to those obtained using Construct B (47.6%; Table 4).

To determine if better restoration capabilities using Construct A were due to higher copy number, fertile (restored) plants were subjected to Southern analysis. The data indicated that there was no bias towards multiple copy integrations among fertile (restored) plants generated using any of the three constructs thereby indicating that the frequency of fertile (restored) plants was a direct reflection of construct efficacy alone. Thus, among the constructs studied, Construct A, containing two different versions of the restorer gene, was found to function more effectively than Construct B (containing a single copy of the wild type gene sequence). All fertile plants thus obtained also showed normal seed set on selfing.

To further ascertain the efficacy of the strategy outlined in the present invention, transgenic barstar plants were generated using a DNA construct (hereafter referred to as Construct I) containing the wild type and modified sequences of the barstar gene under transcriptional control of the TA29 and A9 promoters respectively and the bar gene driven by the CaMV35S double enhancer promoter as a selectable marker. As an appropriate control, transgenic plants were also generated using a DNA construct containing a single copy of the wild type barstar gene under transcriptional control of the TA29 promoter (Construct II). Transformants were selected on media containing Basta (Agrevo). Transgenic plants generated using the above constructs were subjected to Southern analysis to identify single copy events which were subsequently crossed to 4 single copy male sterile barnase lines. F1 progeny derived from the above crosses (40-60 plants/cross) were analyzed for their male fertility/sterility status to determine the restoration abilities of various barstar lines. Results of this study are summarized in Table 5 below. Numbers in each cell represent the number of restorer lines obtained of the total number of barstar lines tested for a given barnase line.

TABLE 5

Restoration profile of barstar transgenic plants

| Construct Code | Barstar constructs | barnase lines | | | | No. of restorers identified/ No. of lines tested |
|---|---|---|---|---|---|---|
| | | bn 3.6 | bn 3.23 | bn 3.4 | bn 3.48 | |
| I | A9-bs(fm) :: TA29-bs(wt) | 8/11 | 6/11 | 7/11 | 4/11 | 25/44 |
| II | TA29 :: bs(wt) | 2/4 | 0/4 | 0/4 | 0/4 | 2/16 |

The above observations conclusively establish that Construct I, containing two different versions of the restorer gene sequence, provides restorer lines at a much greater frequency (25 restorers identified out of 44 lines tested; ~57%) than Construct II (2 of 16 lines tested; ~12%). Furthermore, a greater number of restorer lines could be identified for each barnase line among barstar plants generated using Construct I than those obtained with Constructs II. Of the four barnase lines tested with Construct II, restorers could be identified only for bn 3.6.

Thus, the above results clearly indicate that the method of using two different versions (wild type and modified) of a gene sequence (encoding identical protein products) in the same DNA construct effectively enhances transgene expression levels. It is emphasized here that modifications of the gene sequence as described in this invention can be made for any other gene sequence for both constitutive as well as tissue-specific enhancement in expression using appropriate regulatory elements. Parameters for such modifications can be suitably altered according to the target system in which enhanced expression is desired. The design of the modified barstar gene sequence, its simultaneous use with the corresponding wild type sequence in a DNA construct for enhancing expression of the restorer gene product and the use of the TA29 and A9 promoters as overlapping regulatory elements have been cited merely as a representative example and should not be construed to limit the scope of this invention.

The invention also provides a method to obtain efficient fertility restorer lines for male sterile plants for hybrid seed production. The said method for the development of efficient fertility restorer lines comprises the steps of:
i) transforming the nuclear genome of plant cells with a DNA construct (hereafter referred to as Construct I) comprising:
   a) a first transcription unit comprising the wild type sequence of a restorer gene under transcriptional control of a suitable first tissue-specific promoter (which is used to express the male sterility gene in corresponding male sterile plants) and fused to a suitable transcription termination signal, including a polyadenylation signal.

b) a second transcription unit comprising a modified sequence of the restorer gene, designed in the present study for expression in dicotyledonous crop plants, under transcriptional control of a second tissue-specific promoter and fused to a suitable transcription termination signal including a polyadenylation signal, and c) a third transcription unit comprising a selectable marker gene under transcriptional control of a strong constitutive promoter and fused to a suitable transcription termination signal including a polyadenylation signal.

ii) regenerating plants from said transformed plant cells,
iii) identifying single copy plants by Southern hybridization,
iv) crossing the above single copy plants with male sterile barnase lines,
v) analyzing segregating F1 progeny to identify plants containing the marker gene,
vi) analyzing segregation of male-fertile and male-sterile phenotypes among marker gene-containing F1 progeny to identify putative male sterile-restorer combinations,
vii) molecular analysis of F1 progeny by Tissue-PCR to identify fertility restored plants,
viii) testing pollen viability of fertility restored plants to determine extent of restoration,
ix) selfing the restored plants to obtain F2 progeny
x) analyzing F2 progeny under field conditions for segregation of male-fertile and male-sterile phenotypes to confirm male sterile-restorer combination.

In an embodiment, the preferred restorer gene product is barstar.

In still another embodiment, the preferred first tissue-specific promoter is TA29.

In yet another embodiment, the preferred second tissue-specific promoter is A9.

In another embodiment, the preferred marker gene is bar.

In an embodiment, the preferred constitutive promoter is the CaMV35S promoter with a duplicated enhancer.

In an embodiment, the crop plants used for genetic transformation are selected from dicotyledonous plants, such as *Brassica juncea*.

In another embodiment, the procedure used for development of transformed plants in *Brassica juncea* is *Agrobacterium*-mediated transformation using disarmed Ti plasmid.

In an embodiment, the transgenic plants are analyzed by Southern hybridization to identify transgenic plants containing a single copy of the T-DNA insert.

In yet another embodiment, single copy plants containing the wild type and modified sequences of the restorer gene are crossed with single copy male sterile barnase lines to analyze their restoration capability.

In another embodiment, the F1 progeny obtained from selected backcrossed progeny were transferred to field conditions and tested for stable segregation of male sterility and fertility among maker gene-containing plants.

In an embodiment, fertility restored events among segregating F1 progeny are identified by Tissue PCR.

In another embodiment, fertility restored events were analyzed for pollen viability and selfed to obtain F2 progeny.

In yet another embodiment, F2 progeny grown under field conditions were analyzed for segregation of male-fertility and male-sterility to confirm the male sterile-restorer combination.

The invention is described in detail hereinafter, with reference to the accompanying drawings and examples. Modifications, especially with respect to the DNA construct, its various components viz., the restorer gene(s), tissue-specific promoters, marker genes, constitutive promoters used to express the marker gene and the methods used to deploy the same would be obvious to those skilled in the art. Such modifications are deemed to fall within the scope of this invention and the examples and embodiments provided herein should not be construed as limitations on the inventive concept embodied in this invention.

BRIEF DESCRIPTION OF THE ACCOMPANYING DRAWINGS

In the drawings that accompany the specification

FIG. 1: is a representation of the number of optimal, sub-optimal and rare codons among the wild type and modified barstar gene sequences. The X-axis represents distribution of codons among the wild-type and modified genes. All codons for each amino acid have been categorized (wherever possible) into three classes in accordance with their usage status in plant systems:

(1) Optimal codons: with maximum usage
(2) Sub-optimal codons: with an intermediate usage
(3) Rare codons: with a usage less than 50% of the usage of optimal codons The Y-axis represents the total number of codons in each category. The wild-type barstar gene has 50 optimal codons, 25 sub-optimal codons and 15 rare codons (excluding the termination codon) while the modified sequence has a codon usage consisting of 78 optimal codons and 12 sub-optimal codons. Rare codons have been completely excluded from the modified sequence.

FIG. 2A: is the naturally occurring wild type nucleotide sequence of the barstar gene. (Seq. ID #1). Putative plant intron consensus sequences in the wt gene are highlighted in grey boxes (XXXXXX).

FIG. 2B: is the amino acid sequence of the protein of the naturally occurring wild type barstar gene. (Seq. ID #2)

FIG. 3A: is the modified nucleotide sequence of the barstar gene. (Seq. ID #3)

FIG. 3B is amino acid sequence of the barstar gene whose nucleotide sequence has been modified. (Seq. ID #4). It will be noted that this sequence is same as Seq. ID #2

FIG. 4: is a comparative representation of the wild type (wt) and modified (mod) sequences of the barstar gene. Putative plant intron consensus sequences in the wt gene are highlighted in grey boxes (XXXXXX).

Figure 5:
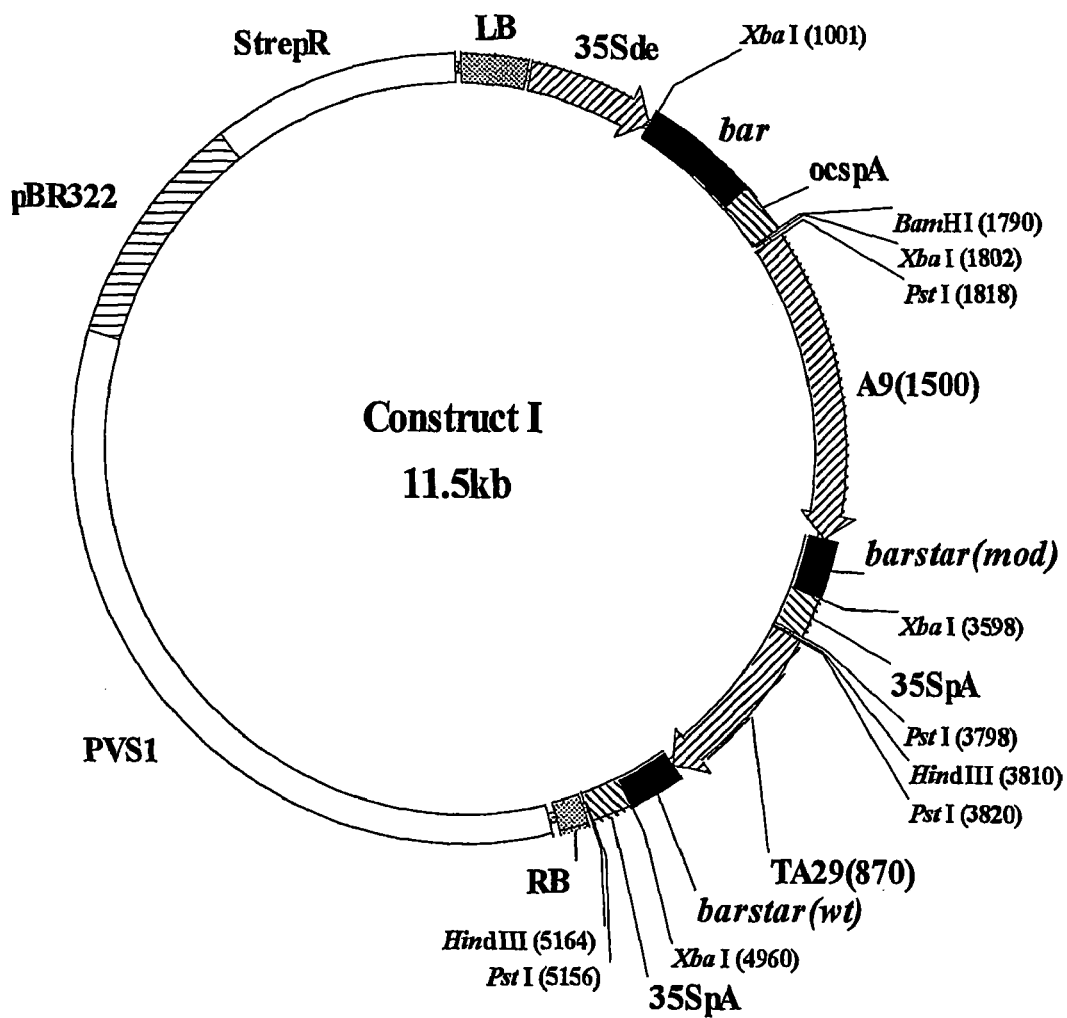

FIG. 5: is a schematic representation of a DNA Construct (Construct I) of the invention depicting various components and locations of restriction enzyme sites. Abbreviations: LB—Left Border of T-DNA of *Agrobacterium tumefaciens*, RB—Right Border of T-DNA of *Agrobacterium tumefaciens*, 35Sde—CaMV35S promoter with duplicated enhancer, bar—coding sequence of the herbicide resistance-conferring bar gene, 35SpA—polyadenylation signal of Cauliflower Mosaic Virus, ocspA—polyadenylation signal of octopine synthase gene, bs(mod)—modified barstar gene, bs(wt)— wild type barstar gene, TA29(870)—870 bp fragment of the tapetum-specific TA29 promoter, A9(1500)—1.5 kb fragment of the A9 promoter.

Figure 6:
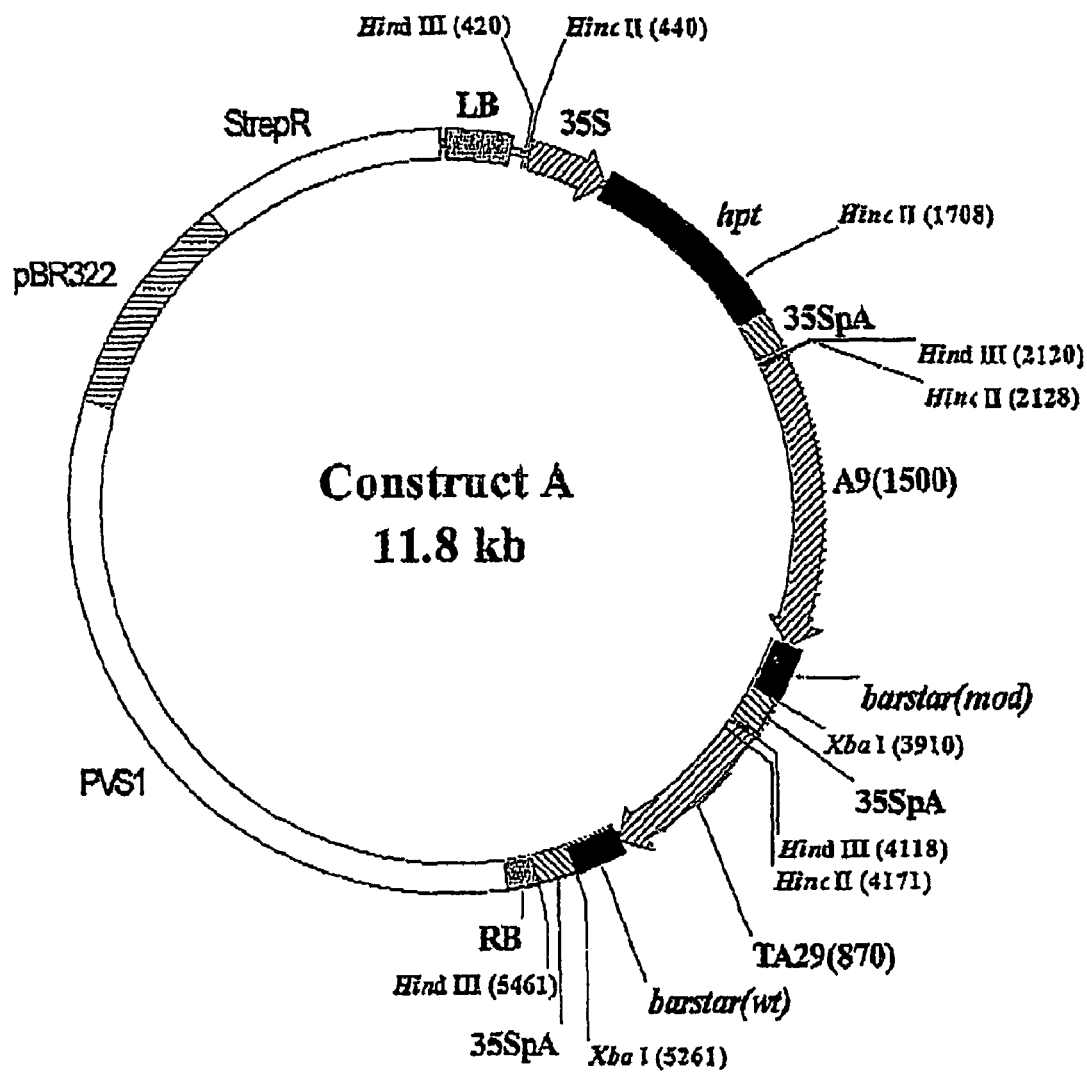

FIG. 6: is a schematic representation of another DNA construct (Construct A) of the invention depicting various components and locations of restriction enzyme sites. Abbreviations: LB—Left Border of T-DNA of *Agrobacterium tumefaciens*, RB—Right Border of T-DNA of *Agrobacteriun tumefaciens*, 35S—CaMV35S promoter with single enhancer, hpt—coding sequence of the hygromycin resistance conferring hpt gene, 35SpA—polyadenylation signal of Cauliflower Mosaic Virus, ocspA—polyadenylation signal of octopine synthase gene, bs(mod)—modified barstar gene, bs(wt)—wild type barstar gene, TA29(870)—870 bp fragment of the tapetum-specific TA29 promoter, A9(1500)—1.5 kb fragment of the A9 promoter.

Figure 7:
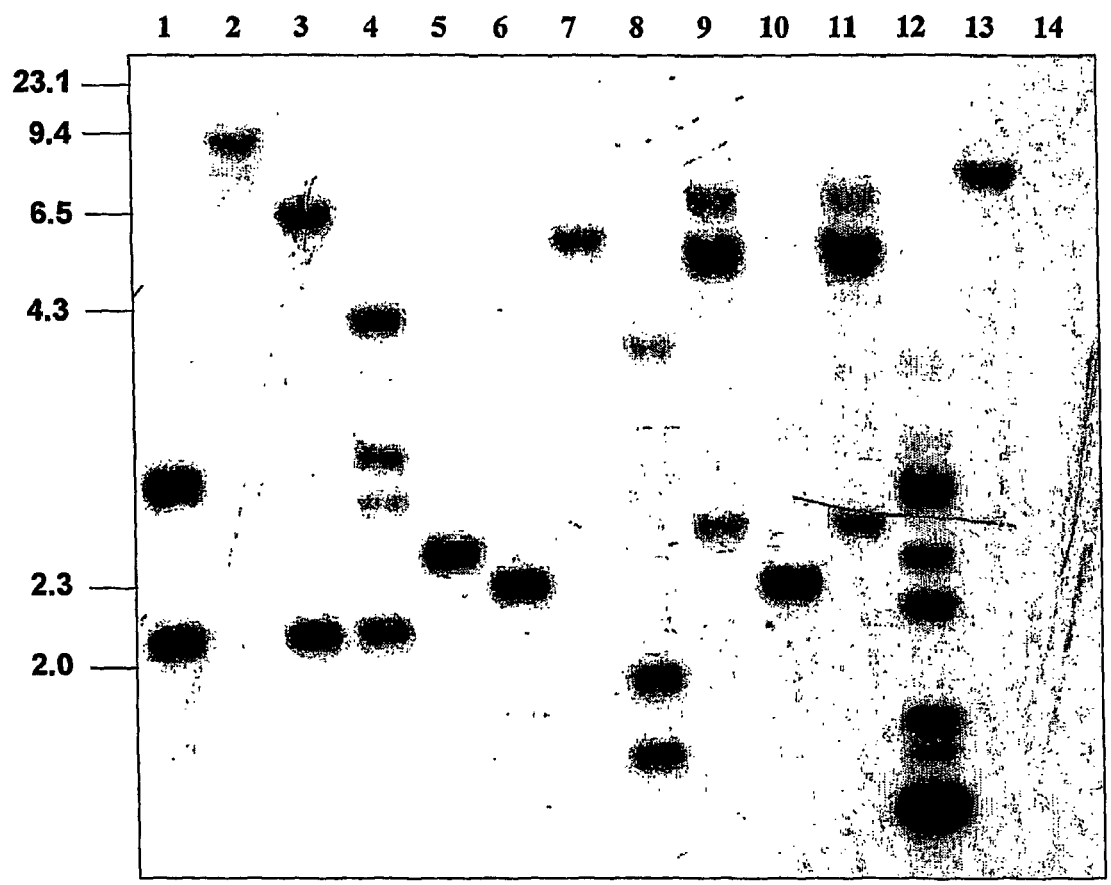

FIG. 7: is a photograph depicting Southern hybridization analysis from the Right Border flank of a representative population of transgenic plants generated using Construct A of the invention. Copy number on the right border flank was determined by probing HincII digests of genomic DNA with the coding sequence of the wild type barstar gene. Lanes 1-13 represent transgenic barstar lines while lane 14 represents an untransformed control plant. The numbers along the left margin of the figure represent a non-linear scale, in kilobase pairs (kb), of DNA fragment sizes.

To discuss in further detail, the invention involves transformation of a plant cell using the DNA constructs (I and A) of the invention comprising two versions of the fertility restorer gene (barstar)—one representing the wild type sequence and the other, a modified sequence for expression in dicotyledonous crop plants—each under independent transcriptional control of regulatory elements with overlapping expression pattern in male reproductive tissues and a marker gene (bar or hpt) under the control of a strong constitutive promoter (CaMV35Sde or CaMV35S) as described in the foregoing sections.

A schematic representation of the Constructs I and A are shown in FIG. 5 and FIG. 6 respectively of the accompanying drawings. The said transformation can be performed employing various vectors and well established procedures such as PEG-mediated direct gene transfer and Electroporation (Bilang et al 1994, In Plant Mol. Biol. Manual, Gelvin and Schilperoot, Eds. Kluwer Academic Publishers), Particle Bombardment (Christou 1994, Plant Mol. Biol. Manual, Gelvin and Schilperoot, Eds. Kluwer Academic Publishers), etc. The applicants recommend the use of Ti-plasmid vectors for genetic transformation of plants because of better control over the process of gene transfer and selection of transgenic plants. In cases of *Agrobacterium*-mediated transformation using disarmed Ti-plasmid vectors, the marker genes are preferably located towards the left border sequence of T-DNA so as to enable selection of transformants carrying the complete T-DNA.

The method outlined in the present application can be used, with appropriate modifications, to enhance tissue-specific as well as constitutive expression of transgenes. In the latter case, the inventors recommend the use of different constitutive promoters to express the wild type and modified versions of the candidate gene(s) to circumvent gene silencing due to promoter homology. Several such constitutive promoters viz., CaMV35S, MAS, OCS, nos, FMV and MMV have been reported in literature. Using the strategy outlined in the present application, the restorer gene, the tissue-specific promoters, the marker gene and the promoter expressing the marker gene can also be used to restore male fertility in a variety of plants wherein transgenic male sterile plants have been generated using molecular methods.

The DNA constructs (I and A) developed in this application are transformed into *Brassica juncea* by *Agrobacterium*-mediated transformation. Transformed shoots are selected on 10 mg/L of phosphinothricin (selective agent for the bar gene) and/or 20 mg/L of hygromycin. Transformed shoots obtained above are transferred to a rooting medium to obtain complete transformed plants, which are subsequently transferred to field conditions and grown to maturity for analysis of their male fertility/sterility status.

Male sterile plants used for restoration studies are characterized by the presence of rudimentary and flattened anthers in flowers with complete absence of pollen production. In contrast, in flowers of untransformed plants and those of restored plants, anthers show pollen production and pollen viability is found to be in the range of 90-100%. The frequency of obtaining restored (fertile) plants (on transformation of male sterile lines) and their pollen viability were used as one of the experimental tools to analyze the efficiency of the (fertility restoration) method described in the present application. As described in the foregoing sections, on transforming a male sterile plant with a construct containing two different versions of the restorer gene sequence—one represented by the naturally occurring wild type sequence and the other modified for expression in dicotyledonous crop plants—each under independent transcriptional control of two overlapping tapetum-specific promoters, the frequency of male sterile plants obtained (89.2%) as well as the percent of fertile plants with pollen viability >90% (65%) were significantly higher as compared to those obtained using constructs containing a single copy or two identical copies of the restorer gene. To further confirm the above observations, transgenic barstar plants were generated using Construct I of the present invention and single copy barstar lines were crossed with male sterile barnase lines to analyze restoration of fertility in F1 progeny. It was found in the above study that the construct based on use of two different versions of the restorer gene sequence provides restorer lines at a much greater frequency (~57%) than constructs containing either two identical copies of the restorer gene (43%) or a single copy of the wild type gene sequence (12%).

The present invention provides a successful method for enhancing transgene expression concomitantly reducing susceptibility of the transgene to post-transcriptional gene silencing. It is important to note that the strategy outlined in the present application can be used with appropriate modifications to enhance both constitutive as well as tissue-specific expression of other candidate genes. Further, it also provides an effective method for the development of efficient fertility restorer lines in crop plants for hybrid seed production using molecular methodologies.

EXAMPLES

Example 1

Construction of Modified Barstar Gene

The 273 bp modified sequence of the barstar gene was constructed by Recursive PCR (Dillon and Rosen 1990, Biotechniques 9:298-299). The modified sequence was assembled in a first PCR reaction (PCR-I) using four long oligos (L1-L4; with an overlap of 20 bp between adjacent oligos) followed by amplification in a second PCR (PCR-II)

of the assembled sequence using two shorter, flanking primers (S1 and S2). Sequences of the oligos and primers used are given below.

```
Oligo L1:
                                            (Seq. ID #5)
5'-ATG AAG AAG GCT GTG ATC AAT GGA GAA CAA ATC AGA
TCT ATC TCA GAC CTT CAT CAA ACT TTG AAG AAG GAG
CTT GCT CTT CCT G-3'

Oligo L2:
                                            (Seq. ID #6)
5'-AAG AGG GTA CTC AAC CCA TCC AGT AAG ACA ATC CCA
CAA AGC GTC CAA GTT CTC ACC ATA GTA CTC AGG AAG
AGC AAG CTC CTT C-3'

Oligo L3:
                                            (Seq. ID #7)
5'-GGA TGG GTT GAG TAC CCT CTT GTT TTG GAA TGG AGG
CAA TTC GAG CAA TCT AAG CAA CTT ACT GAG AAT GGA
GCT GAG AGC GTT CT-3'

Oligo L4:
                                            (Seq. ID #8)
5'-TTA AGA AAG AAT GAT AGT GAT GTC ACA TCC TTC AGC
CTT AGC TTC TCT AAA CAC TTG AAG AAC GCT CTC AGC
TCC ATT-3'

Forward primer (S1):
                                            (Seq. ID #9)
5'-GGC TCG AGC CAC CAT GAA GAA GGC TGT GAT-3'

Reverse primer (S2):
                                            (Seq. ID #10)
5'-CTA GTC TAG ATT AAG AAA GAA TGA TAG TG-3'
```

Optimal reaction conditions used for the assembly of the modified sequence (PCR-I) consisted of 500 ng each of oligos L1-L4, 200 μM each dNTP, 2.5U of Amplitaq DNA polymerase and the supplied buffer at 1× concentration in a final reaction volume of 100 μl. Cycling parameters were as follows: initial denaturation at 94° C., 4 min followed by 4 cycles each of 94° C., 1 min; 55° C., 1 min and 72° C., 1 minute; final extension at 72° C., 5 min. A 1 μl aliquot of PCR-I was taken as the template for the second round of PCR (PCR-II) using the shorter flanking primers, S1 and S2. Reaction conditions for PCR-II consisted of 500 ng each of primers S1 and S2, 200 μM each dNTP, 2.5U of Native Pfu DNA polymerase and the supplied buffer at 1× concentration in a final reaction volume of 100 μl. Cycling parameters were as follows: initial denaturation at 94° C., 4 min followed by 25 cycles each of 94° C., 1 min; 55° C., 1 min and 72° C., 1 minute.

The amplified product was purified and cloned into pCR-Script SK+ at the SrfI site using the pCR-Script SK+ Cloning Kit (Stratagene). Positive clones from two independent amplification reactions were sequenced and were found to contain random mutations in the modified gene sequence. One of the clones containing three single bp additions was subjected to PCR-mediated site-directed mutagenesis to eliminate the point mutations incorporated during gene synthesis. While one of the point mutations was removed by a SOE-ing reaction (Horton 1993, In PCR Protocols: Current Methods and Applications Ed. Bruce A. White, Humana Press), the other two mutations were removed in a simultaneous double mutagenesis reaction by Inverse PCR (Imai et al 1991, Nucl. Acids Res. 19:2785).

For the SOE-ing reaction, two overlapping mutagenizing primers (M1 and M2) each with a single base deletion (corresponding to the added single base mutation) were used in conjunction with the shorter primers, S1 and S2, used earlier for gene synthesis. Sequences of the mutagenic primers are given below:

```
M1   5'-TCC CAC AAA GCG TCC AA-3'     (Seq. ID #11)

M2   5'-TTG GAC GCT TTG TGG GA-3'     (Seq. ID #12)
```

Two independent PCRs (PCR-Is) were performed using primer sets S1-M1 and S2-M2. Optimized reaction conditions for each amplification consisted of 100 ng of template plasmid, 100 pmol of each primer, 200 μM each dNTP, 2.5U of native Pfu DNA polymerase, DMSO to a final concentration of 5% and the supplied buffer at 1× concentration in a final reaction volume of 100 μl. Cycling parameters were as follows: initial denaturation at 94° C., 2 min followed by 28 cycles each of 94° C., 30 sec; 45° C., 30 sec; 72° C., 30 seconds; final extension at 72° C., 5 min. The amplified fragments were gel-purified and 100 ng of each eluted PCR-I product was taken for PCR-II (SOE-ing reaction) with native Pfu DNA polymerase using primers S1 and S2. Optimized reaction conditions for the SOE-ing reaction consisted of 50 pmol of each primer, 200 μM each dNTP, DMSO to a final concentration of 5%, 100 ng of each amplified eluted product from PCR-I, 1.25U of native Pfu DNA polymerase and the supplied buffer at 1× concentration in a final reaction volume of 50 μl. Cycling parameters were as follows: initial denaturation at 94° C. for 2 min followed by 25 cycles each of 94° C., 30 sec; 50° C., 30 sec; 72° C., 30 seconds; final extension at 72° C., 2 min. The amplified product was gel-purified and cloned into pCR-Script SK+ at the SrfI site using the pCR-Script SK+ cloning kit. Four independent clones were sequenced and all were found to have incorporated the desired alteration at the desired position.

For Inverse PCR-mediated mutagenesis, two mutagenizing primers (M3 and M4) were designed such that they were divergent from either side of one of the bases to be deleted; the other deletion to be introduced was incorporated into one of the primers (M4). Sequences of the mutagenizing primers are as follows:

```
M3   5'-CAA GAG GGT ACT CAA CCC ATC CAG (Seq. ID #13)
     TAA GA-3'

M4   5'-TTT GGA AAT GGA GGC AAT TCG AGC (Seq. ID #14)
     AAT CTA A-3'
```

The above primers were used to amplify the entire plasmid (pCR Script SK+ harboring the cloned, synthetic barstar gene) of 3.2 kb. Template DNA used for Inverse PCR was subjected to serial 1:10 dilutions to minimize carryover contamination of template plasmids into the amplified mutagenized product. Reaction conditions consisted of ~2 ng of template DNA, 100 pmol of each primer, 200 μM each dNTP, 5U of Taq DNA polymerase and the supplied buffer at 1× concentration in a final reaction volume of 100 μl. Cycling parameters were as follows: initial denaturation at 94° C. for 4 min followed by 20 cycles each of 95° C., 1 min; 72° C., 30 sec; 72° C., 3 min 20 seconds; final extension at 72° C. for 1 min was also given. PCR products from the above amplification reactions were gel-purified, blunt ended, phosphorylated and self-ligated. Following transformation into E. coli, clones were sequenced to confirm incorporation of the desired mutation.

Following incorporation of the desired modifications in the barstar gene, the synthetic gene was mobilized into appropriate cloning vectors for plant transformation as described below.

Example 2

Development of DNA Constructs

The wild type and modified sequences of the barstar gene were PCR amplified using the following primers to incorporate the restriction sites BspHI and XbaI at their 5' and 3' ends respectively to facilitate further sub-clonings.

Primers for the wild type barstar gene:

```
                                            (Seq. ID #15)
FP:   5'-CCT CAT GAA AAA AGC AGT CAT TAA C-3'
          BspHI (Seq. ID #16)
RP:   5'-GGT CTA GAT TAA GAA AGT ATG ATG GT-3'
          XbaI
```

Primers for the modified barstar gene:

```
                                            (Seq. ID #17)
FP:   5'-CCT CAT GAA GAA GGC TGT GAT CAA-3'
          BspHI (Seq. ID #18)
RP:   5'-CTA GTC TAG ATT AAG AAA GAA TGA TAG TG-3'
           XbaI
```

Following amplification, the PCR products were cloned in pCR Script SK+ at the SrfI site to generate the plasmids pCR Script SK+ barstar(wt) and pCR Script SK+ barstar(mod) and sequenced to verify the fidelity of amplification.

Development of Construct I:
a) The bar gene, used as a plant selectable marker, was fused at its 5' end with the CaMV35S double enhancer promoter (CaMV35Sde) and to a suitable transcription termination/polyadenylation signal at its 3' end.
b) The wild type barstar gene was fused at its 5' end with an 870 bp fragment of the tapetum-specific TA29 promoter and with a suitable transcription termination/polyadenylation signal at its 3' end.
c) The modified barstar gene was fused at its 5' end with the tapetum-specific A9 promoter and at its 3' end with a suitable transcription termination/polyadenylation signal.
d) The components described in (a) to (c) were mobilized into the binary vector pPZP200 as described below:
The CaMV35Sde-bar-ocspA transcription unit was isolated as a PstI-HindIII fragment, blunt ended using Pfu polymerase and cloned at the SmaI site of pPZP200 followed by cloning of the A9(1500)-barstar(fm)-pA transcription unit as a PstI fragment in the PstI site of the same. The TA29(870)-barstar(wt)-pA transcription unit was isolated as a HindIII fragment and cloned at the HindIII site of above binary vector to obtain the final construct.

Development of Construct A:
a) The hpt gene, used as a plant selectable marker, was fused at its 5' end with the CaMV35S promoter (35S) and to a suitable transcription termination/polyadenylation signal at its 3' end.
b) The wild type barstar gene was fused at its 5' end with an 870 bp fragment of the tapetum-specific TA29 promoter and with a suitable transcription termination/polyadenylation signal at its 3' end.
c) The modified barstar gene was fused at its 5' end with the tapetum-specific A9 promoter and at its 3' end with a suitable transcription termination/polyadenylation signal.
d) The components described in (a) to (c) were mobilized into the binary vector pPZP200 as described below:
The A9(1500)-barstar(fm)-pA transcription unit was isolated as a PstI fragment and cloned in the PstI site of the binary vector pPZP200 followed by cloning of the TA29(870)-barstar(wt)-pA transcription unit as a HindIII fragment at the HindIII site of above binary vector. The 35S-hpt-pA transcription unit was isolated as a SacI-SalI fragment and cloned in the corresponding sites of the above binary to develop the final construct.

The final transformation vectors were mobilized into *Agrobacterium tumefaciens* strain GV3101 by electroporation using the BioRad Gene Pulser according to manufacturers' instructions.

Example 3

Seed Sterilization and Germination

Seeds were surface sterilized by treatment in diluted Teepol solution (laboratory grade surfactant) for 10 minutes followed by washing under running water for 30 minutes. Seeds were subsequently treated with 70% ethanol for two minutes under sterile conditions and rinsed twice with sterile distilled water. Further, seeds were treated with 0.05% mercuric chloride for 10 minutes followed by a treatment with 1% sodium hypochlorite for 9 minutes. Following each treatment, seeds were rinsed thoroughly with sterile distilled water. Surface sterilized seeds were germinated on hormone-free full strength MS medium (Murashige and Skoog 1962, Physiol. Plant. 15:473-493). Seeds were germinated in glass tubes covered with a cotton plug with four seeds in each tube. The seeds were kept in dark for two days and then maintained under light (Philips cool-white fluorescent lamps, 2000 lux, 16-h light/8-h dark cycle). Temperature in the culture room was maintained at 23±1° C.

Example 4

*Agrobacterium*-Mediated Genetic Transformation of *Brassica juncea*

Transformation of *Brassica juncea* was performed according to the protocol described by Bade and Damn (1995, In Gene Transfer to Plants, Potrykus and Spangenberg, Eds. Springer Lab Manual) with further modifications. A single bacterial colony harboring the desired construct was inoculated in selective medium containing appropriate antibiotics and grown to saturation. A secondary culture was initiated from the saturated primary culture and grown for 3 hours at 28° C. in non-selective medium. The bacterial cells were subsequently harvested by centrifugation at 5000 rpm for 15 min at 22° C. and resuspended to a final $OD_{600}$ (optical density at 600 nm wavelength) of 0.3 in MS medium containing plant growth hormones, 1 mg/ml BAP (6-benzylaminopurine) and 1 mg/ml NAA (∝-naphthalene acetic acid). This suspension was used for infection of explants. Hypocotyls of 5-day old seedlings of *Brassica juncea* (germinated on an appropriate medium as described above in Example 3) were cut into 5 mm long segments and precultured in aforementioned medium (hereinafter referred to as MSN1B1) for 18 hours at 22° C. with mild shaking at 110 rpm. Following preculture, the medium was decanted and explants were infected for 30 minutes with the bacterial suspension prepared as described earlier. The bacterial suspension was then replaced with MSN1B1 medium and the hypocotyl explants were cultured for 12-14 hours under similar conditions as described above. The explants were subsequently washed with MSN1B1 containing 200 mg/L of the bacteriostatic agent augmentin (to restrict *Agrobacterium* growth) and plated on appropriate selective media.

For transformation of *Brassica juncea* using Construct I (containing the bar gene as a selectable marker), explants were plated on MSN1B1 containing 10 mg/L of phosphinothricin. Regenerated shoots were transferred after six weeks to MS medium containing 2 mg/L IBA (Indole 3-Butyric Acid) for rooting and were maintained as nodal cultures until transplantation.

In case of transformations using Construct A (containing the hpt gene as a selectable marker), hypocotyl explants derived from backcrossed seeds of the male sterile barnase line bn 3.6 (containing the bar gene as a selectable marker) were used. Since the above barnase line contains a single copy of the T-DNA insert, the backcrossed progeny would segregate for phosphinothricin resistance (associated with male sterility) and sensitivity in a 1:1 ratio. Following infection, co-cultivation and washing of explants as described above, explants were plated initially on MSN1B1 medium containing 20 mg/L of the selective agent hygromycin. Regenerating explants were transferred after 25-30 days to MSN1B1 medium containing both the selective agents, hygromycin (20 mg/ml) and phosphinothricin (10 mg/ml). Putative transformed shoots were transferred for rooting on MS medium supplemented with 2 mg/ml IBA, hygromycin (20 mg/L) and phosphinothricin (10 mg/L). Transgenic plants were maintained as nodal cultures until transplantation.

Example 5

Analysis of Male Fertility/Sterility Status and Pollen Viability

Male fertile/sterile plants were identified on the basis of morphological observations of anthers and presence/absence of pollen production. Two to three inflorescence axes from each plant (each inflorescence bearing 10-15 unopened buds) were covered with a pollination bag to test for the formation of selfed seeds. Absence of selfed seeds was taken as a confirmation of male sterility. In plants wherein pollen formation was observed, pollen viability was tested by fluorescein diacetate (FDA) staining according to the protocol described earlier (Heslop-Harrison et al 1984, Theor. Appl. Genet. 67:367-375).

Example 6

Molecular Characterization of Transgenic Plants (a) Isolation of Total DNA:

Total DNA was isolated from fully expanded leaves of transgenic plants (growing in the field under containment conditions) and the untransformed parents following Rogers and Bendich (1994, In Plant Mol. Biol. Manual, Gelvin and Schilperoot, Eds. Kluwer Academic Publishers). One gram of leaf tissue was finely powdered in liquid nitrogen and homogenized in 5 ml extraction buffer containing 100 mM Tris-HCl pH 8.0, 20 mM Sodium EDTA (ethylene diamine tetraacetic acid) pH 8.0, 1.4M Sodium Chloride, 1% PVP40 polyvinyl pyrrolidone 40) and 2% CTAB (Cetyltrimethyl Ammonium Bromide). The above material was incubated at 65° C. with occasional shaking followed by extraction with an equal volume of chloroform:isoamylalcohol. To the supernatant obtained above, 1.25 ml of 10% CTAB solution was added followed by extraction with an equal volume Chloroform: isoamylalcohol. Genomic DNA was precipitated from the above supernatant by addition of three volumes of precipitation buffer (50 mM Tris-HCl pH 8.0, 10 mM Sodium EDTA and 1% CTAB) followed by incubation at room temperature for 30 minutes. The pellet obtained was dissolved in 500 μl of buffer containing 10 mM Tris-HCl pH 8.0, 1 mM Sodium EDTA and 1M NaCl. Undissolved impurities were removed from the above sample by centrifugation followed by precipitation of dissolved DNA using 100% ethanol. The DNA pellet was washed with 70% ethanol and finally dissolved in an appropriate amount of sterile distilled water.

(b) Protocols for Restriction Digestion and Southern Hybridization:

Ten micrograms of total genomic DNA were digested overnight with appropriate restriction enzyme(s) in a 70 μl reaction volume containing 40 units of the restriction enzyme under conditions as recommended by the manufacturers. The digested DNA was electrophoresed on a 0.8% agarose gel at 1.75V/cm for 18-20 hours. Following electrophoresis, the restricted DNA was transferred onto a nylon membrane (Hybond N+, Amersham) by capillary action (for 12-14 hours), air-dried for 45 min and cross-linked in a UV-Crosslinker (Amersham) at $7\times10^4$ joules/cm$^2$. Probes used for hybridization were labeled with $\alpha$-$^{32}$PdCTP or $\alpha$-$^{32}$PdATP by a random priming method using the Megaprime DNA Labeling System (Amersham Pharmacia Biotech). Following hybridization, blots were washed twice in 2×SSC buffer (30 mM sodium chloride and 0.3M sodium citrate, pH 7.6) at 25° C. for 15 min each, followed by one wash at 65° C. for 15 minutes. Stringent washes (wherever necessary) were performed in 0.2×SSC, 0.1% SDS at 65° C. for 15 minutes. The blots were subsequently covered with saran wrap and exposed to X-ray films (Kodak) for 12-24 hours at minus 80° C. Prior to reprobing, blots were deprobed for 40 min in 0.4N NaOH at 42° C. followed by treatment with a neutralization solution (0.2M tris pH 8.0, 0.1×SSC, 0.5% SDS) for 40 min at 42° C.

(c) Analysis of Copy Number:

Transgenic plants generated in *Brassica juncea* were subjected to Southern hybridization to determine copy number of the T-DNA insert and to identify single copy plants for analysis and further studies. Genomic DNA isolated from leaves of transgenic plants generated using DNA Constructs I, II and III were digested with the restriction enzyme BamHI while genomic DNA isolated from leaves of fertile transgenic plants generated by retransformation of the male sterile barnase line bn 3.6 using Constructs A, B and C were initially digested with the enzyme HincII (for copy number determination on the right border flank) followed by digestion of single copy events identified above with XbaI (for determination of copy number on left border flank). Restriction digests were electrophoresed on a 0.8% agarose gel, transferred onto a nylon membrane and cross-linked using a UV-crosslinker. The Southern blots thus generated for Constructs I, II and III were probed with CaMV35Sde promoter for LB and barstar(wt) fragment for RB. while those generated using Constructs A, B and C were probed using the EcoRV-HincII fragment of CaMV35S-hpt-pA cassette representing partial sequences of the CaMV35S promoter and the hpt gene for left border of T-DNA and the right border integration was identified using the barstar(wt) fragment. In all cases, probes used represent DNA sequences derived from both sides of the restriction enzyme site(s) used for digestion of genomic DNA so as to enable determination of copy number on both flanks of the T-DNA.

ADVANTAGES

1) The present invention provides an effective method for enhancing transgene expression in heterologous systems.
2) The present invention provides a novel combination of two sequence versions of a candidate transgene (barstar)—one representing the wild type sequence and the other, a modified sequence designed for expression in dicotyledonous crop plants—with two different overlapping tissue-specific promoters (TA29 and A9), a strong constitutive promoter (CaMV35S with double or single enhancer) and a marker gene (bar or hpt) in a novel construct to enhance transgene expression.
3) The present method relies on the simultaneous use of two different (target) gene sequences encoding identical protein products in the same DNA construct to enhance expression levels. Since the two different gene sequences would transcribe two different RNA molecules, they would effectively circumvent post transcriptional gene silencing due to coding sequence homology.
4) The present method can be effectively used for enhancing constitutive as well as tissue-specific expression of a transgene.
5) The present method provides an effective method for development of efficient restorer lines (by significantly enhancing restorer gene expression) in crop plants for hybrid seed production using molecular methodologies.

The invention claimed is:

1. A DNA construct containing two different coding sequences of a fertility restorer gene, both of which encode the same protein product, the first of said sequences being a naturally occurring wild type gene sequence and the second of said sequences being a modified sequence generated by modification of the wild type sequence using codon degeneracy for expression in crop plants to avoid homology between the modified sequence and the wild type sequence at the DNA and mRNA levels so as to reduce susceptibility to homology-based post-transcriptional gene silencing, said wild type and said modified gene sequences being under the control of first and second tapetum-specific promoters, respectively, wherein said first and second tapetum-specific promoters have overlapping temporal expression patterns in tapetum tissues of said crop plants, wherein said first tapetum-specific promoter is used to express a male sterility gene in corresponding male sterile plants, and wherein expression from said second tapetum-specific promoter begins earlier than said first tapetum-specific promoter.

2. A construct as claimed in claim 1 further comprising:
(i) a first transcription unit comprising the wild type sequence of the restorer gene under transcriptional control of said first tapetum-specific promoter and fused to a transcription termination signal including a polyadenylation signal,
(ii) a second transcription unit comprising a modified sequence of the restorer gene under transcriptional control of said second tapetum-specific promoter and fused to a transcription termination signal including a polyadenylation signal, and
(iii) a third transcription unit comprising a selectable marker gene under transcriptional control of a strong constitutive promoter and fused to a transcription termination signal including a polyadenylation signal.

3. A construct as claimed in claim 2 wherein the restorer gene is a sequence encoding a protein capable of inhibiting or negating the cytotoxic effects of another protein generated by a lethal gene sequence.

4. A construct as claimed in claim 2 wherein the restorer gene encodes a protein selected from the group consisting of barstar and protease inhibitors.

5. A construct as claimed in claim 1 wherein said crop plants are dicotyledonous plants.

6. A construct as claimed in claim 1 wherein said crop plants are monocotyledonous plants.

7. A construct as claimed in claim 5 wherein said first wild type gene is a barstar gene comprising the nucleotide sequence as shown in SEQ ID NO: 1.

8. A construct as claimed in claim 7 wherein said second modified gene is a modified barstar gene comprising the sequence as shown in SEQ ID NO: 3.

9. A construct as claimed in claim 2 wherein tapetum-specific promoters of the first and second transcription units are selected from the group consisting of TA29, A9, tap1, and bcp1 promoters.

10. A construct as claimed in claim 2 wherein the first tapetum-specific promoter is a TA29 promoter, and the second tapetum-specific promoter is an A9 promoter.

11. A construct as claimed in claim 2 wherein the selectable marker gene is selected from the group of herbicide resistance-conferring genes consisting of bar gene, ALS gene and tfdA gene, or from the group of antibiotic resistance-conferring genes consisting of nptII gene, hpt gene and aadA gene.

12. A construct as claimed in claim 2 wherein the strong constitutive promoter for expression of the selectable marker gene is selected from the group consisting of CaMV35S single enhancer promoter, CaMV35S double enhancer promoter, mirabilis mosaic virus (MMV) promoter, and figwort mosaic virus (FMV) promoter.

13. A fertility restorer transgenic plant, or parts or seeds thereof, each of which contain in their nuclear genome the construct of claim 2.

14. The transgenic plant as claimed in claim 13 which is selected from the group consisting of dicotyledonous plants and monocotyledonous plants.

15. The plant as claimed in claim 14 wherein said dicotyledonous plant is *Brassica juncea*.

16. A method to obtain efficient fertility restorer lines in crop plants for hybrid seed production, said method comprising:
i) regenerating transformed crop plants from plant cells transformed with a DNA construct containing two different coding sequences of a barstar fertility restorer gene both of which encode the same protein product, the first of said sequences being a naturally occurring wild type gene sequence and the second of said sequences being a modified sequence generated by modification of the wild type sequence using codon degeneracy for expression in dicotyledonous crop plants to avoid homology between the modified sequence and the wild type sequence at the DNA and mRNA levels so as to reduce susceptibility to homology-based post-transcriptional gene silencing, said DNA construct comprising:
  a) a first transcription unit comprising the wild type sequence of the barstar restorer gene under transcriptional control of a first tapetum-specific promoter, which promoter is used to express a male sterility gene in corresponding male sterile plants, wherein said restorer gene sequence is fused to a transcription termination signal, including a polyadenylation signal,
  b) a second transcription unit comprising a modified sequence of the barstar restorer gene under transcriptional control of a second tapetum-specific promoter and fused to a transcription termination signal including a polyadenylation signal, and
  c) a third transcription unit comprising a selectable marker gene under transcriptional control of a strong constitutive promoter and fused to a transcription termination signal including a polyadenylation signal;
  wherein the first and second tapetum-specific promoters have overlapping temporal expression patterns in tapetal tissues of said crop plants;
  wherein said first tapetum-specific promoter is used to express a male sterility gene in a corresponding male sterile plant; and
  wherein expression from said second tapetum-specific promoter begins earlier than said first tapetum-specific promoter,
(ii) identifying transformed crop plants having a single copy of the DNA construct,
(iii) crossing the above single copy plants with male sterile barnase lines,
(iv) subjecting the F1 progeny obtained from crosses between barnase and barstar lines to molecular analysis to identity fertility restored plants, and
(v) testing pollen viability of fertility restored plants to determine extent of restoration.

17. The method as claimed in claim 16 wherein said crop plants are dicotyledonous plants.

18. The method as claimed in claim 17, wherein said dicotyledonous plant is *Brassica juncea*.

19. The method as claimed in claim 18, wherein said restorer lines in *Brassica juncea* are generated by *Agrobacterium*-mediated transformation using disarmed Ti plasmid.

20. The method as claimed in claim 16 wherein said transformed plants having a single copy of said DNA construct are identified by Southern hybridization.

21. The method as claimed in claim 16 wherein prior to said molecular analysis of said F1 progeny, said F1 progeny are analysed and segregated to identify plants containing the marker gene, and said marker gene containing F1 plants are analysed for segregation of male-fertile and male-sterile phenotypes on the basis of pollen production and selfed seed formation.

22. The method as claimed in claim 16 wherein subsequent to said testing of pollen viability of fertility restorer plants, the restored plants are self pollinated to obtain F2 progeny.

23. The method as claimed in claim 16 wherein said F2 progeny are analysed under field conditions for segregation of male fertile and male sterile phenotypes to confirm the male sterile-restorer combination.

24. The method as claimed in claim 16 wherein said first wild type gene comprises the nucleotide sequence as shown in SEQ ID NO: 1.

25. The method as claimed in claim 24 wherein said second modified gene comprises the sequence as shown in SEQ ID NO: 3.

26. The method as claimed in claim 16 wherein the first tapetum-specific promoter is a TA29 promoter.

27. The method as claimed in claim 16 wherein the second tapetum-specific promoter is an A9 promoter.

28. The method as claimed in claim 16 wherein the marker gene is bar gene.

29. The method as claimed in claim 16 wherein the constitutive promoter is CaMV35S double enhancer promoter.

30. The method as claimed in claim 16 wherein said crop plants are monocotyledonous plants.

* * * * *